United States Patent
Yoshida

(10) Patent No.: US 10,980,514 B2
(45) Date of Patent: Apr. 20, 2021

(54) ULTRASONIC DEVICE UNIT, ULTRASONIC PROBE, AND ULTRASONIC APPARATUS

(71) Applicant: Seiko Epson Corporation, Tokyo (JP)

(72) Inventor: Kazuki Yoshida, Fujimi (JP)

(73) Assignee: Seiko Epson Corporation

( * ) Notice: Subject to any disclaimer, the term of this patent is extended or adjusted under 35 U.S.C. 154(b) by 479 days.

(21) Appl. No.: 15/922,107

(22) Filed: Mar. 15, 2018

(65) Prior Publication Data

US 2018/0271488 A1 Sep. 27, 2018

(30) Foreign Application Priority Data

Mar. 22, 2017 (JP) .............................. JP2017-055814

(51) Int. Cl.
  *A61B 8/00* (2006.01)
  *H05K 1/18* (2006.01)
  *H05K 1/02* (2006.01)
  *A61B 8/06* (2006.01)

(52) U.S. Cl.
  CPC .......... *A61B 8/4455* (2013.01); *A61B 8/4427* (2013.01); *H05K 1/028* (2013.01); *H05K 1/189* (2013.01); *A61B 8/06* (2013.01); *A61B 8/4494* (2013.01); *A61B 8/461* (2013.01); *A61B 8/54* (2013.01); *H05K 2201/09063* (2013.01)

(58) Field of Classification Search
  CPC .............. A61B 8/4483; B06B 2201/20; B06B 2201/55
  See application file for complete search history.

(56) References Cited

U.S. PATENT DOCUMENTS

| | | | |
|---|---|---|---|
| 8,229,142 B2 * | 7/2012 | Colaizzi | G10K 9/122 381/190 |
| 2006/0119760 A1 | 6/2006 | Okuda | |
| 2010/0103637 A1 * | 4/2010 | Jin | A61B 8/4494 361/777 |

FOREIGN PATENT DOCUMENTS

| | | |
|---|---|---|
| CN | 1782790 A | 6/2006 |
| JP | 2006-235349 A | 9/2006 |
| JP | 2016-092592 A | 5/2016 |

\* cited by examiner

*Primary Examiner* — Jason M Ip

(74) *Attorney, Agent, or Firm* — Harness, Dickey & Pierce, P.L.C.

(57) ABSTRACT

An ultrasonic device unit includes an ultrasonic device having a device-side terminal, a reinforcing plate having a support adapted to support the ultrasonic device, and a flexible printed wiring board to be connected to the ultrasonic device, the flexible printed wiring board is provided with a connection to be connected to the device-side terminal, and a bend continuous with the connection, extending away from the ultrasonic device, and having an end edge parallel to an extending direction, and the reinforcing plate is provided with a bending guide provided to a first side parallel to a first direction crossing the extending direction, having a circular arc curved surface convex away from the support, and opposed to the bend, and a guide surface disposed at an end in the first direction of the bending guide, and adapted to guide the end edge of the bend.

10 Claims, 14 Drawing Sheets

ULTRASONIC DEVICE UNIT, ULTRASONIC PROBE, AND ULTRASONIC APPARATUS

BACKGROUND

1. Technical Field

The present invention relates to an ultrasonic device unit, an ultrasonic probe, and an ultrasonic apparatus.

2. Related Art

In the past, there has been known a wiring structure for connecting a flexible printed wiring board (a flexible board) to an electric component (see, e.g., JP-A-2016-92592 (Document 1)).

The ultrasonic device unit of Document 1 is provided with the ultrasonic device having terminals corresponding respectively to the ultrasonic elements, and the ultrasonic device is connected to a device terminal via a flexible printed wiring board (a flexible board).

The flexible board is provided with a first flat-plate part disposed on one end side with respect to the center line, and the ultrasonic device is fixed to the first flat-plate part. Further, the flexible board is provided with a second flat-plate part disposed on the other end side with respect to the center line, and connecters to which the terminals of the ultrasonic device are connected are disposed in the second flat-plate part. Further, by bending the flexible board so as to overlap the second flat-plate part and the first flat-plate part, the size of the flexible board is made to coincide with the size of the ultrasonic device.

Incidentally, in an ultrasonic probe for performing transmission or reception of an ultrasonic wave, it is required to dispose the ultrasonic device in a limited space in the housing. Here, in the flexible board described in Document 1, the flexible board is connected to the ultrasonic device, and the flexible board is bent so as to overlap the ultrasonic device. However, in the case in which the bending direction of the flexible board is tilted with respect to the direction of the end side of the ultrasonic device, apart of the flexible board fails to overlap the ultrasonic device to project to the outside of the end side of the ultrasonic device, and thus, it becomes difficult to store the flexible board in the limited space.

SUMMARY

An advantage of some aspects of the invention is to provide an ultrasonic device unit, an ultrasonic probe, and an ultrasonic apparatus miniaturization of which can be achieved with a simple configuration.

An ultrasonic device unit according to an application example of the invention includes an ultrasonic device having a device-side terminal, a reinforcing plate having a support part adapted to support the ultrasonic device, and a flexible printed wiring board to be connected to the ultrasonic device, the flexible printed wiring board is provided with a connection part to be connected to the device-side terminal, and a bending part continuous with the connection part, extending in a direction of getting away from the ultrasonic device, and having an end edge parallel to an extending direction, and the reinforcing plate is provided with a bending guide part provided to a first side parallel to a first direction crossing the extending direction, having a circular arc curved surface convex toward a direction of getting away from the support part, and opposed to the bending part, and a guide surface disposed at an end part in the first direction of the bending guide part, and adapted to guide the end edge of the bending part.

In the application example, when connecting the connection part of the flexible printed wiring board to the device-side terminal of the ultrasonic device, the bending part continuous with the connection part is opposed to the bending guide part provided to the first side of the reinforcing plate, and at the same time, it becomes possible for the end edge of the bending part to have contact with the guide surface provided to the end part of the bending guide part. Therefore, by curving the bending part of the flexible printed wiring board along the bending guide part, breaking of the interconnections in the bending part can be prevented. Further, by disposing the end edge of the bending part along the guide surface, it is possible to prevent the disadvantage that the bending part is curved in a direction tilted with respect to the first side. Further, it is possible to prevent the disadvantage that a part of the flexible printed wiring board projects outside the outer edge of the reinforcing plate, and thus, the miniaturization of the ultrasonic device unit can be achieved.

In the ultrasonic device unit according to the application example, it is preferable that in the extending direction, an end part on an opposite side to the support part of the guide surface is located on a side getting away from the support part with respect to a projection tip of the bending guide part.

In the application example with this configuration, the guide surface projects toward the extending direction from the bending guide part. Therefore, when curving the bending part along the bending guide part, it is possible to always make the guide surface guide the end edge of the bending part. Therefore, it is possible to appropriately bend the bending part along the first side.

In the ultrasonic device unit according to the application example, it is preferable that the reinforcing plate has a rectangular shape having a third side parallel to the first direction, and a second side and a fourth side crossing the first side and the third side and being parallel to the extending direction, and provided with reference corner parts, each provided with a first reference surface parallel to the first direction and a second reference surface parallel to the extending direction, and disposed in at least three of corner parts where one of the first side and the third side and one of the second side and the fourth side cross each other, and the reference corner parts are each provided with the guide surface disposed on a surface crossing the first side.

In the application example with this configuration, there are provided at least three reference corner parts each provided with the guide surface. According to such a configuration, when fixing the ultrasonic device unit to a predetermined position in the electronic apparatus, it is possible to achieve positioning with the first reference surface and the second reference surface of each of the reference corner parts.

In the ultrasonic device unit according to the application example, it is preferable that the flexible printed wiring board is provided with a slit including the end edge of the bending part and an opposed edge opposed to the end edge in an opening edge of the slit, and a width dimension in a direction parallel to the first direction from the end edge to the opposed edge of the slit is one of equal to and larger than a width dimension in the first direction of the reference corner part.

In the application example with this configuration, there is provided a slit having a slit width equal to or larger than the width dimension in the first direction of the reference corner part. Therefore, when making the guide surface guide the end edge of the bending part, the reference corner part is inserted through the slit. Therefore, it is possible to prevent the interference between the flexible printed wring board and the reference corner part.

In the ultrasonic device unit according to the application example, it is preferable that the reinforcing plate is formed of a resin material, and is provided with a recessed part on a reverse surface on an opposite side to a surface provided with the support part, and the recessed part is provided with a metal plate.

According to the application example with this configuration, since the reinforcing plate is formed of the resin material, short circuit does not occur in the interconnections provided to the flexible printed wiring board. On the other hand, if the reinforcing plate is formed of the resin material, the reinforcing plate becomes low in strength. In contrast, in the application example with the configuration described above, a metal plate is disposed in the recessed part of the reinforcing plate, namely a position where the metal plate does not have contact with the flexible printed wiring board, and the strength of the reinforcing plate can be increased by the metal plate.

An ultrasonic probe according to another application example of the invention preferably includes any of the ultrasonic devices described above, and a housing adapted to store the ultrasonic device unit.

In the ultrasonic probe according to the application example, such an ultrasonic device unit as described above is housed in the housing, and by making the ultrasonic probe have contact with the test object, the ultrasonic measurement on the test object can be performed. Further, as described above, in the ultrasonic device unit, the flexible printed wiring board can be bent along the first side of the ultrasonic device while preventing the breaking of the interconnections, and therefore easily deformed into a compact shape suitable for space-saving. Therefore, it is possible to appropriately arrange the ultrasonic device unit within the limited space of the ultrasonic probe, and further, the miniaturization of the ultrasonic probe can also be achieved.

In the ultrasonic probe according to the application example, it is preferable that the reinforcing plate has a rectangular shape having a third side parallel to the first direction, and a second side and a fourth side crossing the first side and the third side and being parallel to the extending direction, and provided with reference corner parts, each provided with a first reference surface parallel to the first direction and a second reference surface parallel to the extending direction, and the guide surface disposed on a surface crossing the first side, and disposed in at least three of corner parts where one of the first side and the third side and one of the second side and the fourth side cross each other, and the housing is provided with a unit hold part having contact with the first reference surfaces and the second reference surfaces.

According to the application example with this configuration, by making the first reference surfaces and the second reference surfaces of the reference corner parts have contact with the corner parts or the like of the unit hold part, it is possible to appropriately position (fit) the ultrasonic device unit to the unit hold part of the housing.

An ultrasonic apparatus according to another application example of the invention includes any of the ultrasonic device units described above, and a control section adapted to control the ultrasonic device unit.

In the application example, by controlling such an ultrasonic device unit as described above, it is possible to perform a variety of types of ultrasonic processing (e.g., ultrasonic measurement on the test object, and ultrasonic therapy on the test object) in accordance with the measurement result of the ultrasonic measurement. Further, since the ultrasonic device unit can be miniaturized as describe above, the miniaturization of the ultrasonic apparatus can also be achieved.

BRIEF DESCRIPTION OF THE DRAWINGS

The invention will be described with reference to the accompanying drawings, wherein like numbers reference like elements.

DESCRIPTION OF AN EXEMPLARY EMBODIMENT

An embodiment according to the invention will hereinafter be described.

Figure 1:
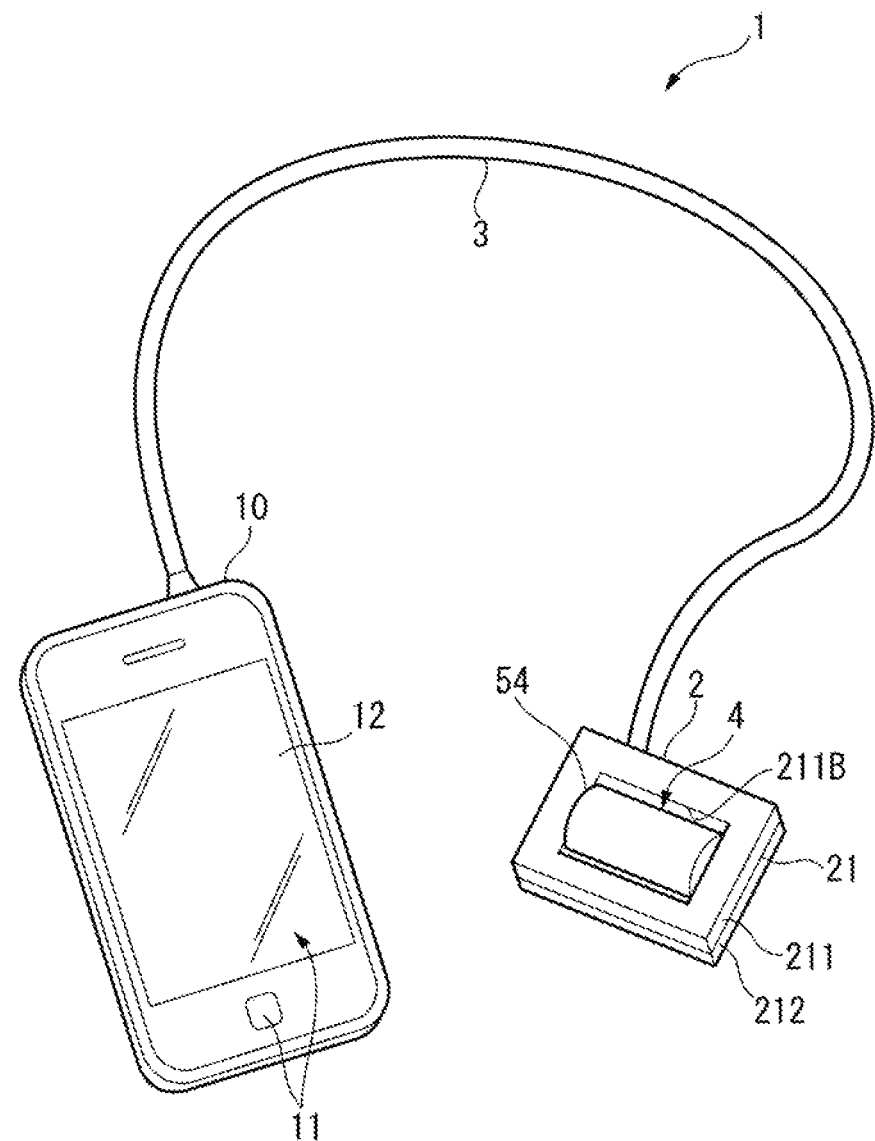
FIG. 1 is a perspective view showing a schematic configuration of an ultrasonic measurement apparatus according to an embodiment of the invention.

FIG. 1 is a perspective view showing a schematic configuration of the ultrasonic measurement apparatus 1.

As shown in FIG. 1, the ultrasonic measurement apparatus 1 corresponds to an ultrasonic apparatus, and is provided with an ultrasonic probe 2, and a control device 10 electrically connected to the ultrasonic probe 2 via a cable 3.

The ultrasonic measurement apparatus 1 transmits an ultrasonic wave from the ultrasonic probe 2 to the inside of a living body (e.g., a human body) in the state in which the ultrasonic probe 2 has contact with a surface of the living body. Further, the ultrasonic measurement apparatus 1 receives the ultrasonic wave reflected by an organ in the living body using the ultrasonic probe 2, and then, for example, obtains an internal tomographic image of the inside of the living body to measure the state (e.g., blood flow) of the organ in the living body based on the received signal.

1. Configuration of Control Device

As shown in FIG. 1, for example, the control device 10 corresponds to a control section, and is provided with an operating section 11 including buttons or a touch panel, and a display section 12. Further, although not shown in the drawings, the control device 10 is provided with a storage section formed of a memory and so on, and an arithmetic section constituted by a central processing unit (CPU) and so on. The control device 10 makes the arithmetic section execute a variety of programs stored in the storage section to thereby control the ultrasonic measurement apparatus 1. For example, the control device 10 outputs a command for controlling the drive of the ultrasonic probe 2, forms an image of the internal structure of the living body and then makes the display section 12 display the image, and measures the living body information such as the blood flow to make the display section 12 display the living body information based on the received signal input from the ultrasonic probe 2. As such a control device 10, there can be used a terminal device such as a tablet terminal, a smartphone, or a personal computer, and a dedicated terminal device for operating the ultrasonic probe 2 can also be used.

2. Configuration of Ultrasonic Probe

Figure 2:
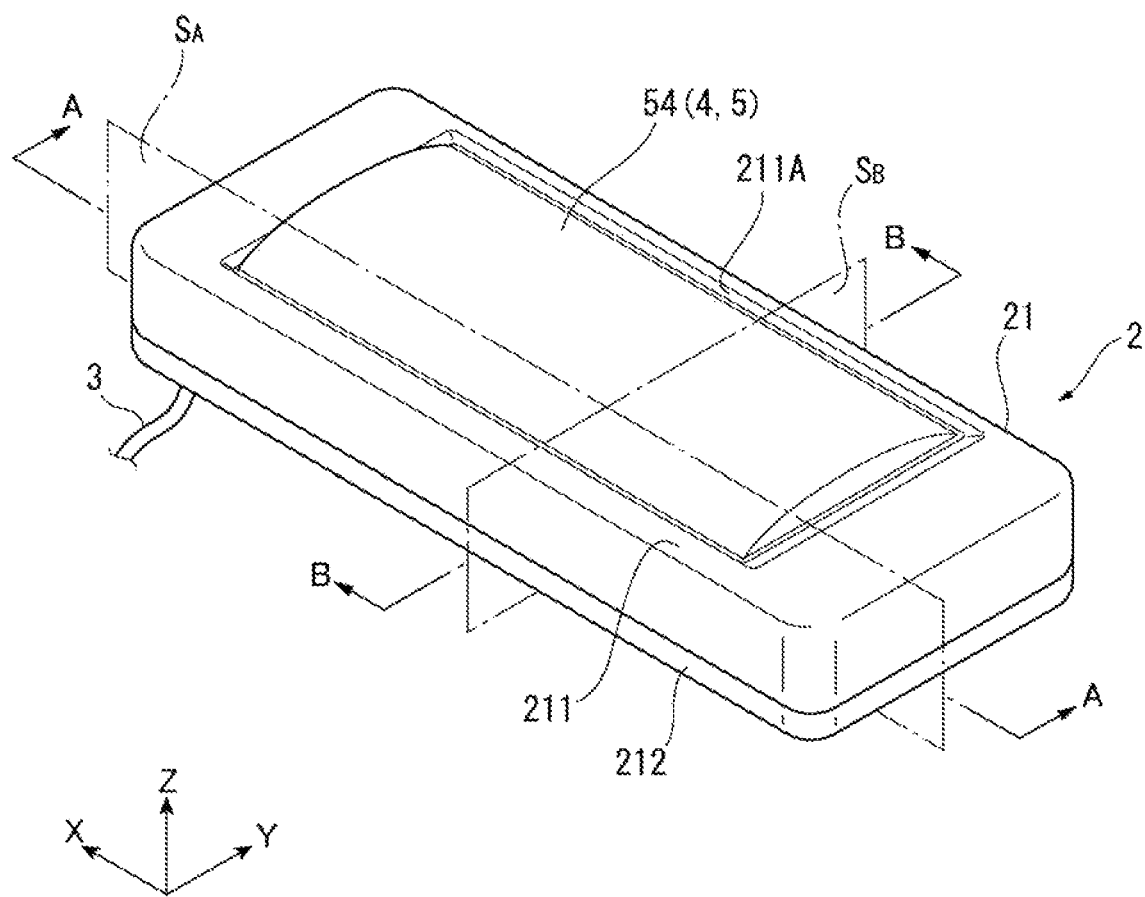
FIG. 2 is a perspective view showing an appearance of an ultrasonic probe according to the embodiment.
Figure 3:
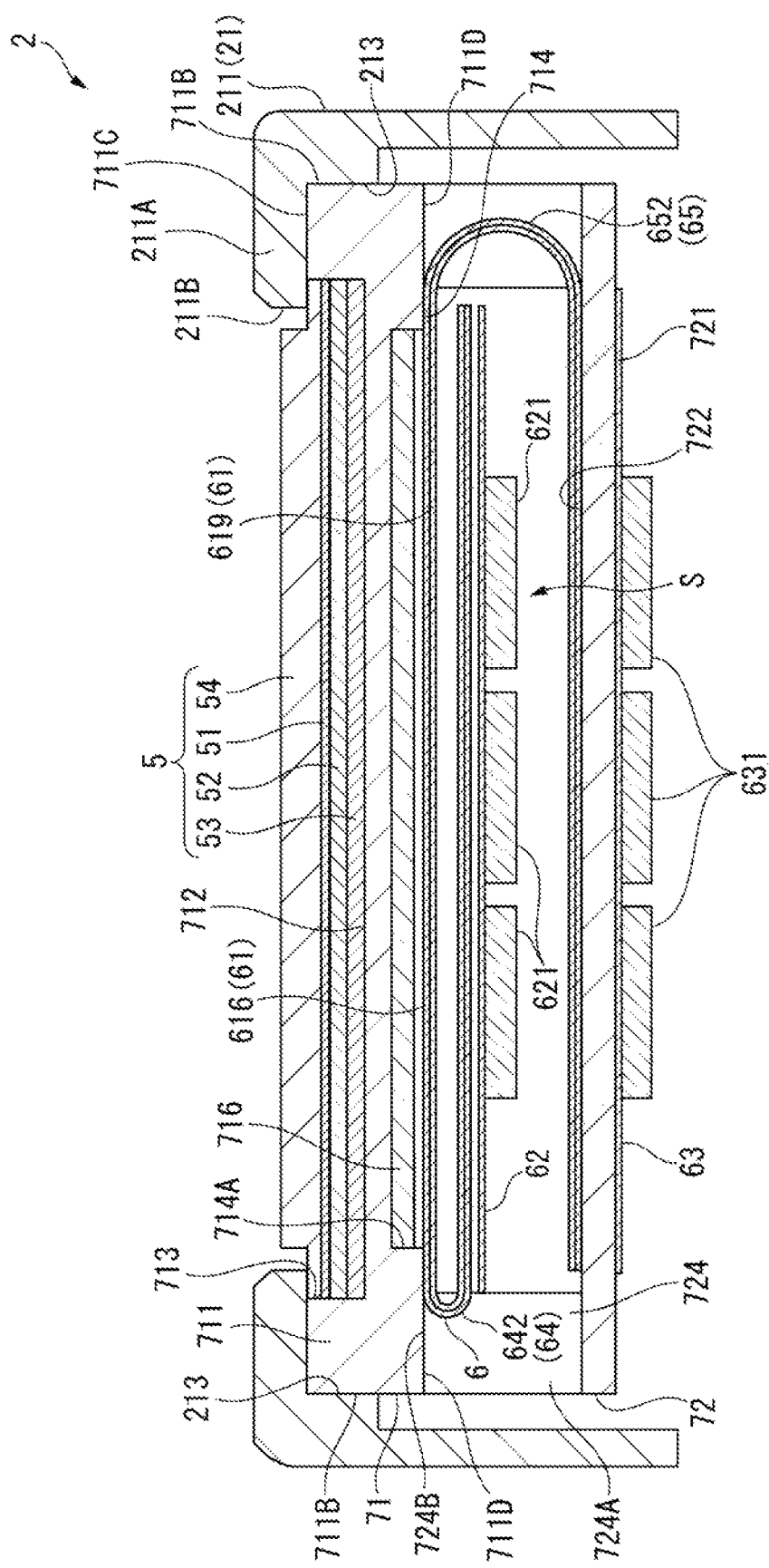
FIG. 3 is a cross-sectional view of the ultrasonic probe cut along the line A-A shown in FIG. 2.
Figure 4:
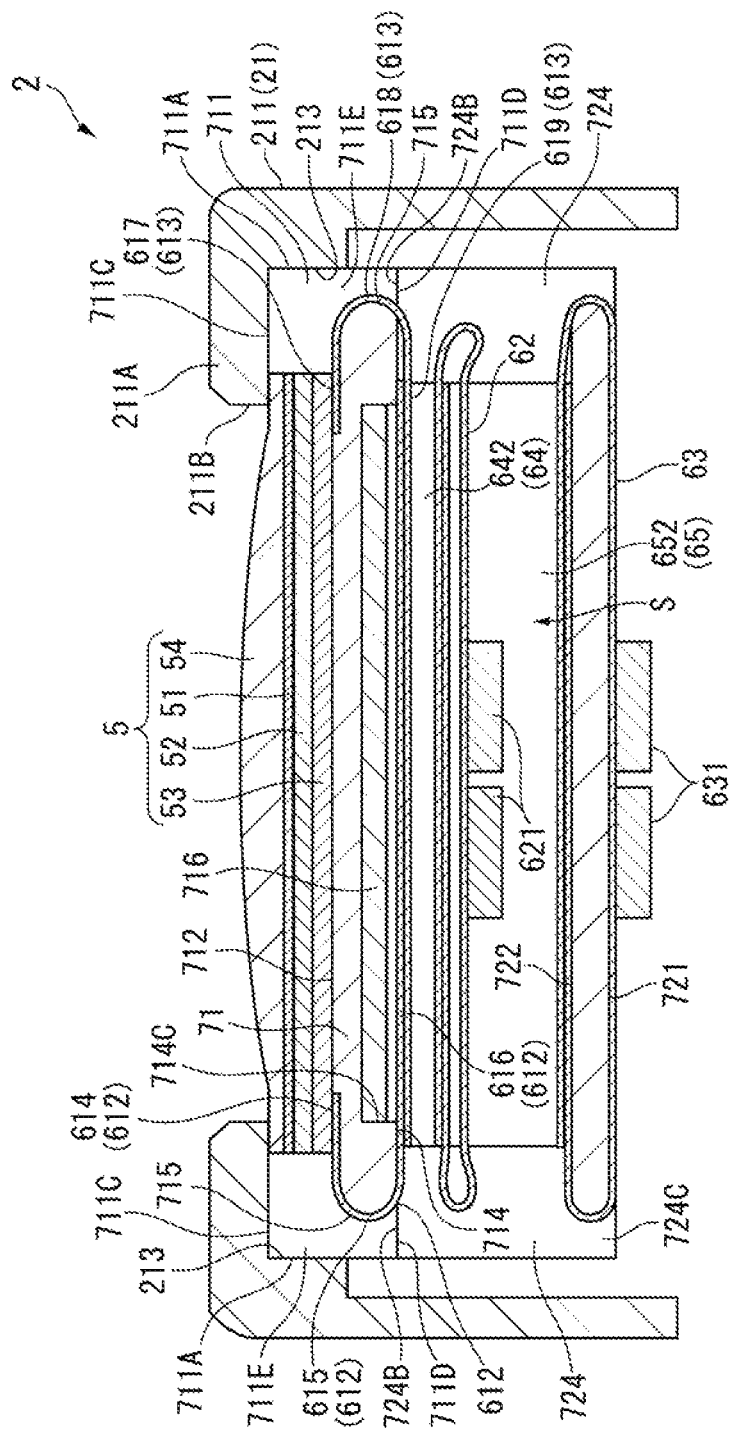
FIG. 4 is a cross-sectional view of the ultrasonic probe cut along the line B-B shown in FIG. 2.

FIG. 2 is a perspective view showing an appearance of the ultrasonic probe 2. FIG. 3 is a cross-sectional view of the ultrasonic probe 2 cut along the line A-A (a plane $S_A$) shown in FIG. 2, and FIG. 4 is a cross-sectional view of the ultrasonic probe 2 cut along the line B-B (a plane $S_B$) shown in FIG. 2.

The ultrasonic probe 2 corresponds to an ultrasonic probe, and is provided with a housing 21, and an ultrasonic device unit 4 stored inside the housing 21 as shown in FIG. 1 through FIG. 4. Further, the ultrasonic device unit 4 is configured including an ultrasonic device 5, a flexible printed wiring board (a flexible board 6), a first reinforcing plate 71, and a second reinforcing plate 72.

Hereinafter, each of the constituents will be described in detail.

2-1. Configuration of Ultrasonic Device 5

As shown in FIG. 3 and FIG. 4, the ultrasonic device constituting the ultrasonic device unit 4 includes an ultrasonic substrate 51, a sealing plate 52, a wiring board 53, and an acoustic lens 54, and is formed by stacking the wiring board 53, the sealing plate 52, the ultrasonic substrate 51, and the acoustic lens 54 in this order. In the present embodiment, the ultrasonic device 5 is formed to have, for example, a rectangular shape in a planar view viewed from the stacking direction (a Z direction) of the wiring board 53, the sealing plate 52, the ultrasonic substrate 51, and the acoustic lens 54.

2-1-1. Configuration of Ultrasonic Substrate 51

Figure 5:
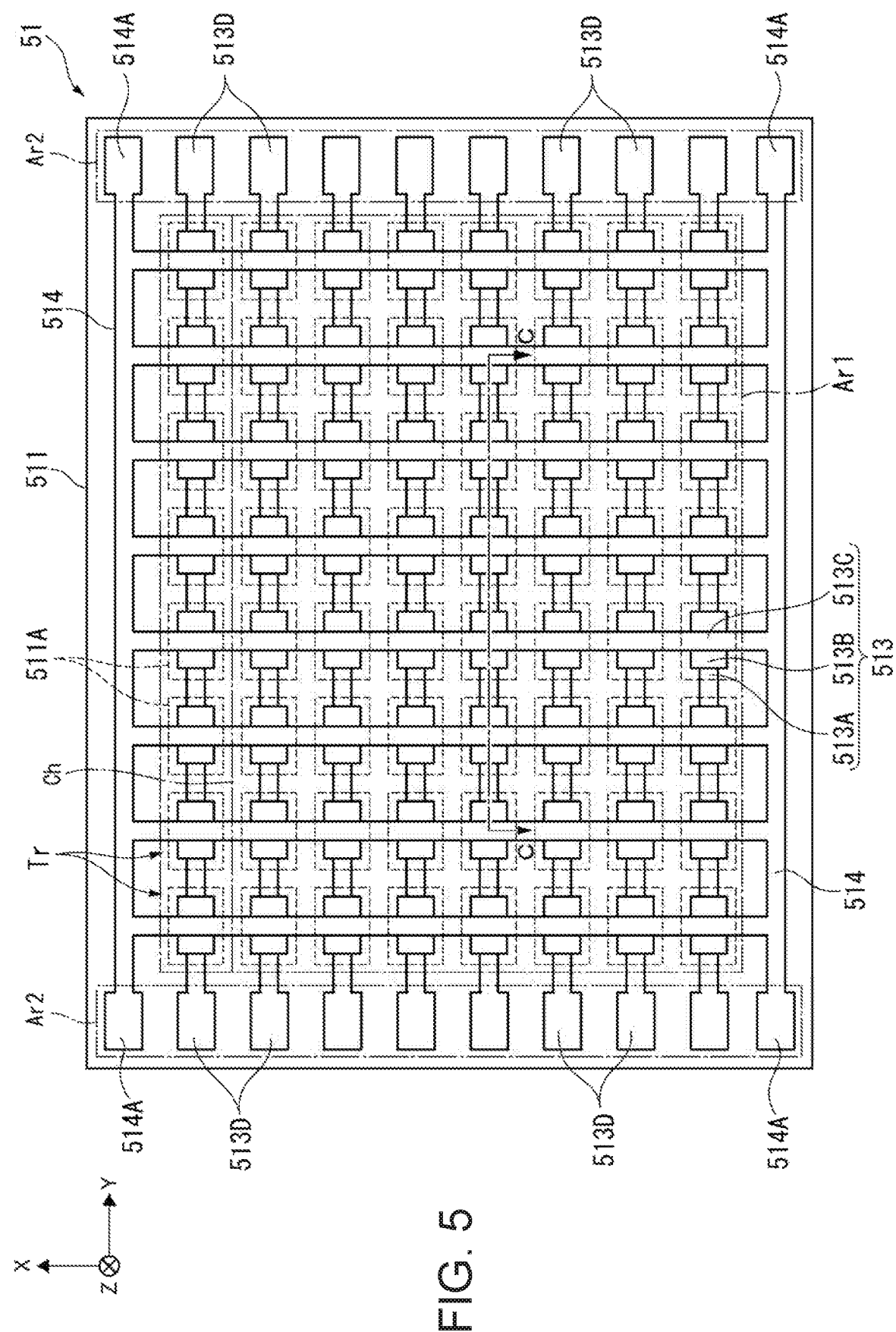
FIG. 5 is a plan view showing a schematic configuration of an ultrasonic substrate of the embodiment.

FIG. 5 is a plan view showing a schematic configuration of the ultrasonic substrate 51 of the present embodiment.

As shown in FIG. 5, the ultrasonic substrate 51 is provided with a plurality of ultrasonic transducers Tr arranged in a two-dimensional array along the X direction (a second direction, a scanning direction) and the Y direction (a first direction, a slicing direction). In the present embodiment, 1-CH (channel) transmission/reception column Ch (vibrator element) is constituted by a plurality of ultrasonic transducers Tr (ultrasonic elements) arranged in the Y direction. Further, a plurality of the 1-CH transmission/reception columns Ch arranged side by side along the X direction constitutes the ultrasonic substrate 51 having a two-dimensional array structure. Here, in the ultrasonic substrate 51, an area where the ultrasonic transducers Tr are arranged is defined as an array area Ar1.

It should be noted that in FIG. 5, the number of the ultrasonic transducers Tr arranged is reduced for the sake of convenience of explanation, but in reality, there are arranged a larger number of ultrasonic transducers Tr.

Figure 6:
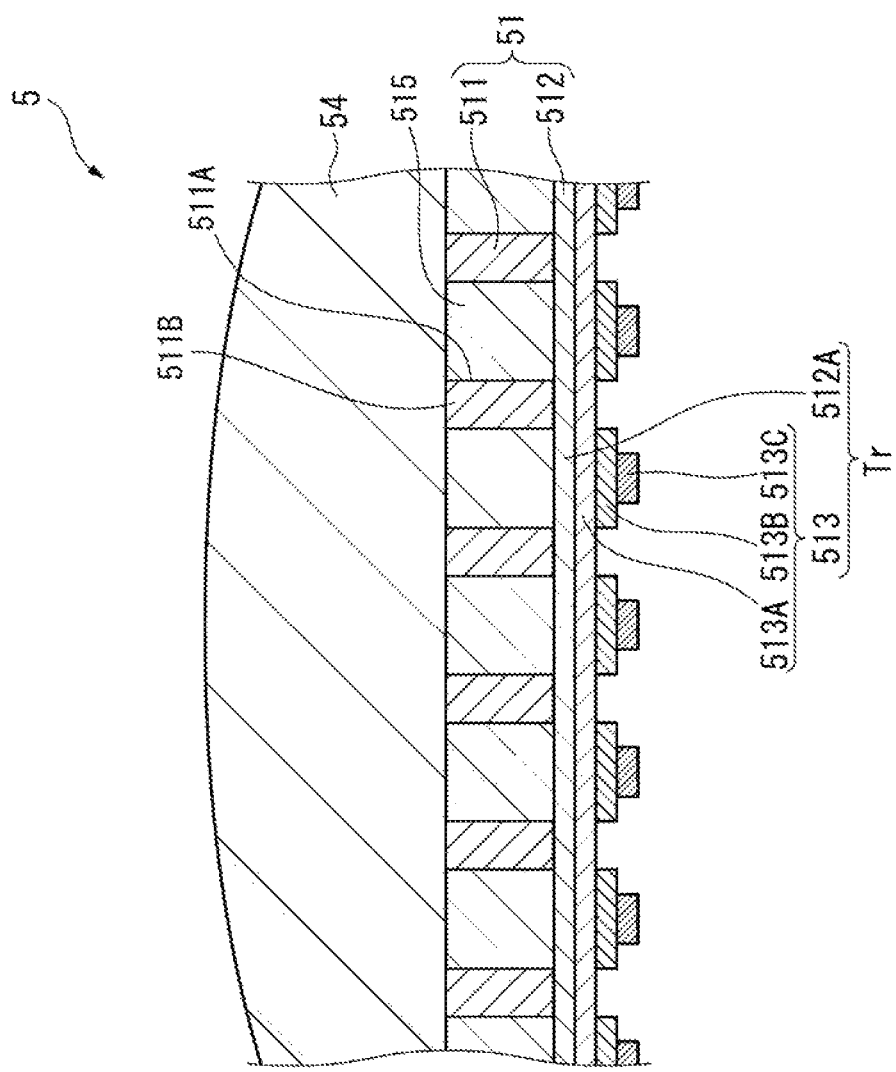
FIG. 6 is a cross-sectional view of the ultrasonic substrate cut along the line C-C shown in FIG. 5.

FIG. 6 is a schematic cross-sectional view of the ultrasonic substrate 51 cut along the line C-C shown in FIG. 5.

As shown in FIG. 6, the ultrasonic substrate 51 is configured including an element substrate 511, a support film 512 disposed on the element substrate 511, and piezoelectric elements 513 disposed on the support film 512.

The element substrate 511 is formed of a semiconductor substrate made of, for example, Si. The element substrate 511 is provided with substrate opening parts 511A corresponding to the respective ultrasonic transducers Tr. In the present embodiment, each of the substrate opening parts 511A is a through hole penetrating the element substrate 511 in the thickness direction thereof, and the support film 512 is disposed on one end side (the sealing plate 52 side) of the through hole.

Further, the side of the substrate opening part 511A where the support film 512 is not provided is filled with an acoustic layer 515 having acoustic impedance approximate to that of the living body.

Further, on a surface of the element substrate 511 located on the opposite side to the support film 512, there is disposed the acoustic lens 54 having contact with the element substrate 511 and the acoustic layer 515. The acoustic lens 54 is a part which is exposed from the sensor window 211B (see FIG. 1 and so on) provided to the housing 21 when the ultrasonic device unit 4 is stored in the housing 21, and forms a part to have contact with the test object when performing the ultrasonic measurement. Similarly to the acoustic layer 515, the acoustic lens 54 is formed of, for example, silicone having acoustic impedance approximate to that of the living body, and is formed to have a cylindrical shape with an axis parallel to the X direction.

The support film 512 is formed of, for example, a stacked body of $SiO_2$ and $ZrO_2$, and is disposed so as to cover the entire area on the sealing plate 52 side of the element substrate 511. Specifically, the support film 512 is supported by partition walls 511B constituting the substrate opening parts 511A, and closes the sealing plate 52 side of the substrate opening parts 511A. The thickness dimension of the support film 512 is made sufficiently small with respect to that of the element substrate 511.

It should be noted that in the present embodiment, the support film 512 is formed by performing a thermal oxidation treatment on one surface of the element substrate 511 formed of Si to form $SiO_2$, and then stacking $ZrO_2$ thereon. On this occasion, by performing etching on the element substrate 511 using the support film 512 including $SiO_2$ as an etching stopper, it becomes possible to easily form the substrate opening parts 511A and the partition walls 511B.

The piezoelectric elements 513 are disposed on respective parts of the support film 512 closing the respective substrate opening parts 511A. The piezoelectric elements 513 are each formed of, for example, a stacked body obtained by stacking a lower-part electrode 513A, a piezoelectric film 513B, and an upper-part electrode 513C from the support film 512 side.

Here, the part of the support film 512 closing the substrate opening part 511A constitutes a vibrating part 512A, and the vibrating part 512A and the piezoelectric element 513 constitute one ultrasonic transducer Tr.

In such an ultrasonic transducer Tr, by applying a rectangular-wave voltage (a drive voltage) having a predetermined frequency between the lower-part electrode 513A and the upper-part electrode 513C, the piezoelectric film 513B is deflected to vibrate the vibrating part 512A to transmit the ultrasonic wave. Further, when the vibrating part 512A is vibrated by the ultrasonic wave (a reflected wave) reflected by the living body, an electrical potential difference occurs between an upper part and a lower part of the piezoelectric film 513B. Thus, by detecting the electrical potential difference occurring between the lower-part electrode 513A and the upper-part electrode 513C, it becomes possible to detect the ultrasonic wave received.

As shown in FIG. 5, in the present embodiment, the lower-part electrode 513A is formed along the Y direction to have a linear shape, and connects the plurality of ultrasonic transducers Tr constituting the 1-CH transmission/reception column Ch to each other. Drive terminals 513D therefor are electrically connected to the wiring board 53 via, for example, through electrodes provided to the sealing plate 52.

Further, the upper-part electrode 513C is formed along the X direction to form a linear shape, and connects the ultrasonic transducers Tr arranged in the X direction. Further, the end parts on the ±X sides of the upper-part electrode 513C are respectively connected to common electrode lines 514. The common electrode lines 514 each connect the upper-part electrodes 513C arranged along the Y direction to each other, and are each provided with common terminals 514A at the end parts thereof, wherein the common terminals 514A are electrically connected to the wiring board 53. The common terminals 514A are electrically connected to the wiring board 53 via, for example, through electrodes provided to the sealing plate 52.

2-1-2. Configuration of Sealing Plate 52

The sealing plate 52 is formed so that the planar shape of the sealing plate 52 viewed from the thickness direction has the same shape as that of, for example, the ultrasonic substrate 51. Further, the sealing plate 52 is bonded with a fixation member such as resin on the support film 512 side of the ultrasonic substrate 51, and at the positions overlapping the partition walls 511B viewed from the substrate thickness direction, to reinforce the ultrasonic substrate 51.

The sealing plate 52 is provided with openings not shown at positions opposed to the drive terminals 513D and the common terminals 514A of the element substrate 511, and through electrodes 521 (see FIG. 7), for example, for connecting the drive terminals 513D and the common terminals 514A to the wiring board 53 are inserted through the openings.

2-1-3. Configuration of Wiring Board 53

Figure 7:
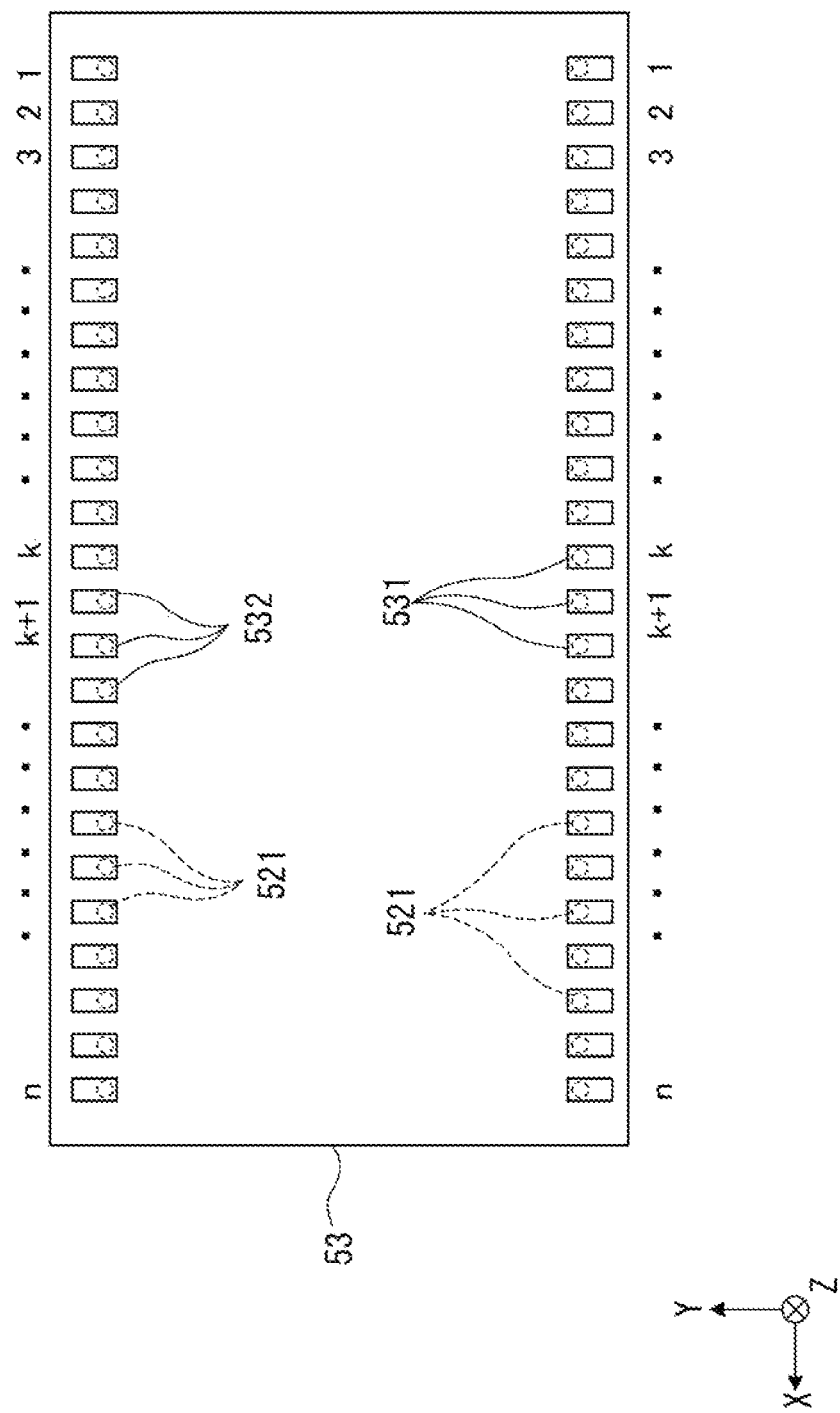
FIG. 7 is a plan view showing a schematic configuration of a wiring board of the embodiment.

FIG. 7 is a plan view showing a schematic configuration of the wiring board 53.

As shown in FIG. 7, the wiring board 53 is provided with device-side terminals (first device-side terminals 531 and second device-side terminals 532) at positions opposed to the drive terminals 513D and the common terminals 514A. These device-side terminals are connected to the drive terminals 513D and the common terminals 514A via the through electrodes 521 provided to the sealing plate 52, respectively.

In the present embodiment, the drive terminals 513D and the common terminals 514A are disposed in the both end parts (Ar2) of the flexible board 6 in the Y direction as shown in FIG. 5. Therefore, also in the wiring board 53, the device-side terminals corresponding to the drive terminals 513D and the common terminals 514A are disposed in the both end parts in the Y direction. Here, the device-side terminals disposed on the −Y side are referred to as first device-side terminals 531, and the device-side terminals disposed on the +Y side as the other end side in the Y direction are referred to as second device-side terminals 532.

Further, in the present embodiment, the number of each of the first device-side terminals 531 and the second device-side terminals 532 provided to the wiring substrate 53 is n (n is an integer equal to or greater than 2). Here, the first device-side terminal disposed at the −X side end part is defined as a 1-st first device-side terminal 531, the second device-side terminal disposed at the −X side end part is defined as a 1-st second device-side terminal 532, the first device-side terminal disposed at the +X side end part is defined as an n-th first device-side terminal 531, and the second device-side terminal disposed at the +X side end part is defined as an n-th second device-side terminal 532. The first device-side terminal 531 and the second device-side terminal 532 disposed at "i"-th position from the −X side end part are defined as an i-th first device-side terminal 531 and an i-th second device-side terminal 532, respectively.

To each of the first device-side terminals 531 and the second device-side terminals 532, there is connected the flexible board 6.

2-2. Configuration of Flexible Printed Wiring Board (Flexible Board 6)

Figure 8:
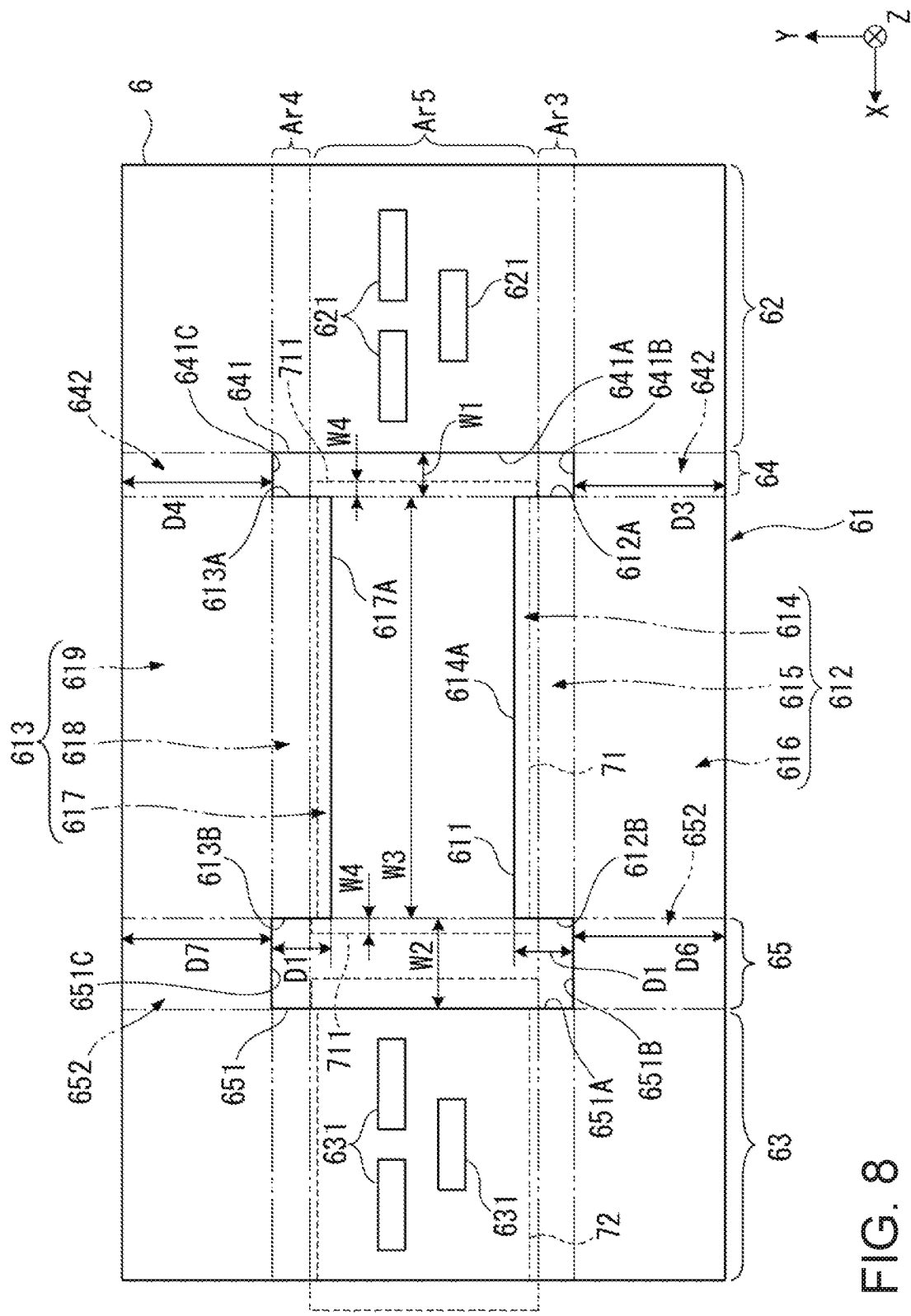
FIG. 8 is a plan view showing a schematic configuration of a surface of a flexible board of the embodiment.
Figure 9:
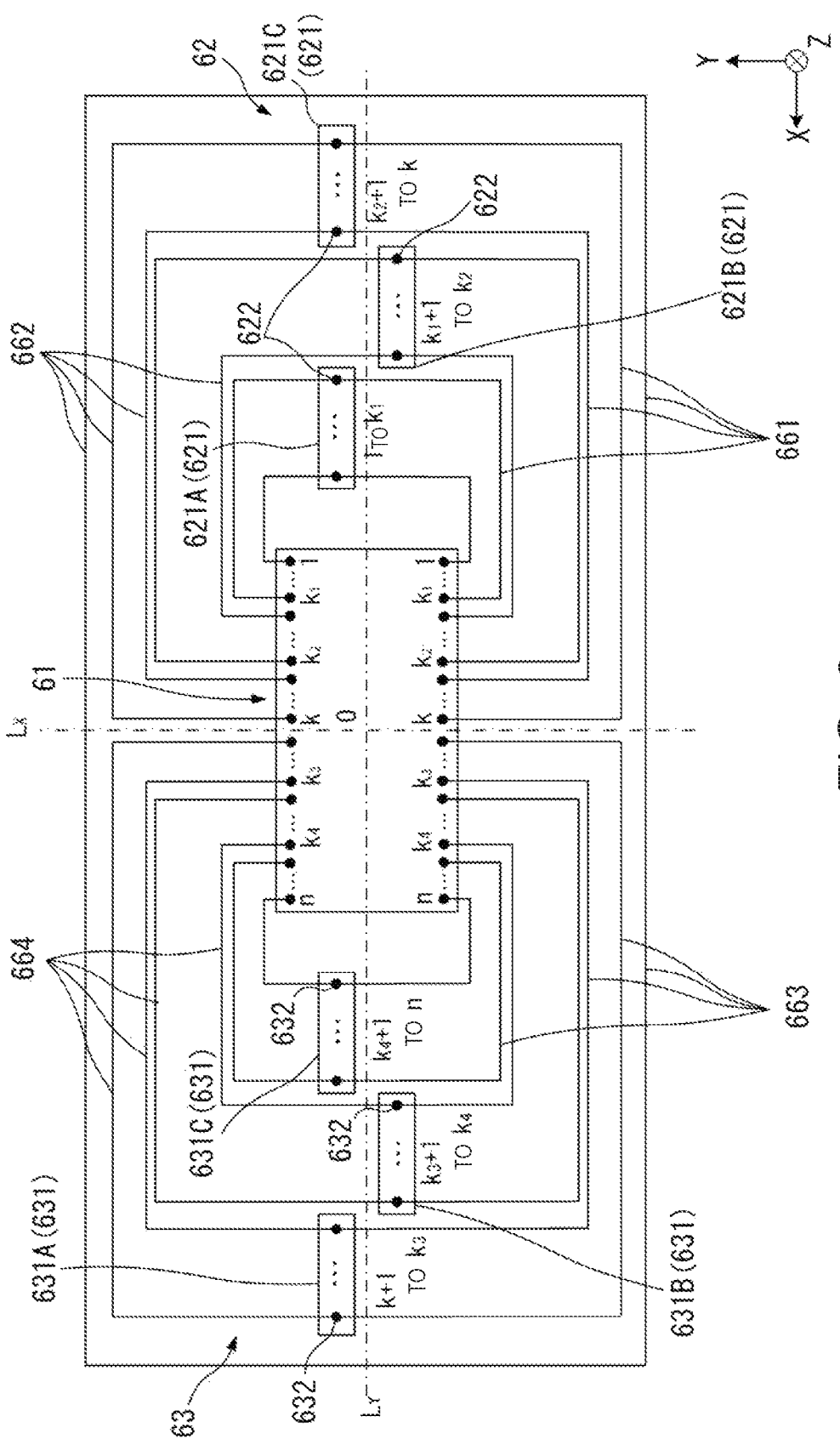
FIG. 9 is a diagram showing a wiring structure of the flexible board of the embodiment.

FIG. 8 is a plan view showing a schematic configuration of a surface of the flexible board 6 of the present embodiment. FIG. 9 is a diagram showing a wiring structure of the flexible board.

As shown in FIG. 8, the flexible board 6 is formed to have, for example, a rectangular planar shape. The flexible board 6 is divided into five regions along the X direction.

Specifically, the flexible board 6 is provided with a device connection section 61 disposed in the central part in the X direction, a first connector section 62 located on the −X side of the device connection section 61, and a second connector section 63 located on the +X side of the device connection section 61. Further, the device connection section 61 and the first connector section 62 are linked (connected) to each other via a first inflective part 64, and the device connection section 61 and the second connector section 63 are linked (connected) to each other via a second inflective part 65.

2-2-1. Description of Device Connection Section 61

The device connection section 61 is a part to which the ultrasonic device 5 is connected, and has an opening part 611 having a roughly rectangular shape corresponding to the acoustic lens 54. Further, the device connection section 61 is configured including a first wiring part 612 disposed on the −Y side of the opening part 611, and a second wiring part 613 disposed on the +Y side of the opening part 611.

The first wiring part 612 is a part in which interconnections to be connected to the first device-side terminals 531 are disposed, and is provided with a first connection part 614, a first bending part 615, and a first device stacking part 616.

The first connection part 614 has connection terminals disposed in a connection side 614A along the X direction facing the opening part 611, and connected to the respective first device-side terminals 531 along the connection side 614A.

The first bending part 615 is a part extending from the first connection part 614 toward the −Y side (in an extending direction). Although the details will be described later, the first bending part 615 is opposed to a bending guide part 715 (see FIG. 4 and so on) provided to the first reinforcing plate 71 when bending the flexible board 6.

Further, an end edge (a first negative-side end edge 612A) on the −X side of the first connection part 614 and the first bending part 615 constitutes a part of an opening edge of a first slit 641 provided to the first inflective part 64 described later. Further, an end edge (a first positive-side end edge 612B) on the +X side of the first connection part 614 and the first bending part 615 constitutes apart of an opening edge of a second slit 651 provided to the second inflective part 65 described later.

The first device stacking part 616 is a part which overlaps the first reinforcing plate 71 when connecting the flexible board 6 to the ultrasonic device 5 supported by the first reinforcing plate 71, and bending the flexible board 6 around the first bending part 615 along the first reinforcing plate 71.

In the present embodiment, as shown in FIG. 9, the interconnections (first interconnections 661) connected to the 1-st through k-th first device-side terminals 531 out of the first device-side terminals 531 are disposed in the first device stacking part 616 so as to extend toward the first connector section 62. Meanwhile, the interconnections (third interconnections 663) connected to the (k+1)-th through n-th first device-side terminals 531 out of the first device-side terminals 531 are disposed in the first device stacking part 616 so as to extend toward the second connector section 63.

The second wiring part 613 is a part in which interconnections to be connected to the second device-side terminals 532 are disposed, and has substantially the same configuration as that of the first wiring part 612. Specifically, the second wiring part 613 is configured line symmetrically with the first wiring part 612 about a Y-central axis line $L_Y$ passing through the central point in the Y direction of the opening part 611 and parallel to the X direction.

Specifically, the second wiring part 613 is provided with a second connection part 617, a second bending part 618, and a second device stacking part 619.

The second connection part 617 has connection terminals disposed along a connection side 617A along the X direction facing the opening part 611, and connected to the respective second device-side terminals 532 along the connection side 617A.

The second bending part 618 is a part extending from the second connection part 617 toward the +Y side (in an extending direction), and is opposed to the bending guide part 715 of the first reinforcing plate 71 described later when bending the flexible board 6.

An end edge (a second negative-side end edge 613A) on the −X side of the second connection part 617 and the second bending part 618 constitutes a part of an opening edge of the first slit 641 provided to the first inflective part 64 described later. Further, an end edge (a second positive-side end edge 613B) on the +X side of the second connection part 617 and the second bending part 618 constitutes a part of the opening edge of the second slit 651 provided to the second inflective part 65 described later.

The second device stacking part 619 is a part which overlaps the first reinforcing plate 71 together with the first device stacking part 616 when connecting the flexible board 6 to the ultrasonic device 5 fixed to the first reinforcing plate 71, and bending the second bending part 618 of the flexible board 6 along the first reinforcing plate 71.

Among the interconnections disposed in the second device stacking part 619, the interconnections (second interconnections 662) to be connected to the 1-st through k-th second device-side terminals 532 are disposed so as to extend toward the first connector section 62. Further, the interconnections (fourth interconnections 664) to be connected to the (k+1)-th through n-th second device-side terminals 532 are disposed so as to extend toward the second connector section 63.

2-2-2. Description of First Connector Section 62 and Second Connection Section 63

The first connector section 62 and the second connector section 63 are disposed on the ±X sides of the device connection section 61, respectively, and has a width dimension smaller than the width dimension in the X direction of the device connection section 61.

The first connector section 62 is provided with a plurality of connectors 621 each provided with a plurality of external connection terminals 622 (see FIG. 9), and the second connector section 63 is provided with a plurality of connectors 631 each provided with a plurality of external connection terminals 632 (see FIG. 9). As shown in FIG. 8 and FIG. 9, in the present embodiment, the first connector section 62 is provided with the three connectors 621, and the second connector section 63 is provided with the three connectors 631. Further, each of the connectors 621 is provided with the external connection terminals 622 to be connected to either of the interconnections 661, 662, and each of the connectors 631 is provided with the external connection terminals 632 to be connected to either of the interconnections 663, 664.

It should be noted that although in the present embodiment, there is shown an example in which the three connectors 621 (631) are provided, this is not a limitation, and it is also possible to provide one or two connectors 621 (631), or it is also possible to provide four or more connectors 621 (631).

Here, among the three connectors 621 provided to the first connector section 62, in the connector 621A located on the +X side, there are disposed the 1-st external connection terminal 622 through the $k_1$-th ($k_1 < k$) external connection terminal 622. Further, in the connector 621A, the 1-st external connection terminal 622 is disposed at the +X side end part, and the $k_1$-th external connection terminal 622 is disposed at the −X side end part.

Among the three connectors 621 provided to the first connector section 62, in the connector 621B located in the central part in the X direction, there are disposed the $(k_1+1)$-th external connection terminal 622 through the $k_2$-th ($k_1 < k_2 < k$) external connection terminal 622. Further, in the connector 621B, the $(k_1+1)$-th external connection terminal 622 is disposed at the +X side end part, and the $k_2$-th external connection terminal 622 is disposed at the −X side end part.

Among the three connectors 621 provided to the first connector section 62, in the connector 621C located on the −X side, there are disposed the ($k_2$+1)-th external connection terminal 622 through the k-th external connection terminal 622. Further, in the connector 621C, the ($k_2$+1)-th external connection terminal 622 is disposed at the +X side end part, and the k-th external connection terminal 622 is disposed at the −X side end part.

Therefore, in the first connector section 62, the "i ($1 \le i \le k$)"-th external connection terminal 622 from the +X side corresponds to the i-th external connection terminal.

Further, to the i-th external connection terminal 622, there are connected the first interconnection 661 connected to the i-th first device-side terminal 531, and the second interconnection 662 connected to the i-th second device-side terminal 532.

Here, the first interconnection 661 and the second interconnection 662 disposed in the first connector section 62 are made roughly line-symmetric about the Y-central axis line $L_Y$ similarly to the device connection section 61. In other words, the wiring length from the first device-side terminal 531 to the external connection terminal 622 in the first interconnection 661 and the wiring length from the second device-side terminal 532 to the external connection terminal 622 in the second interconnection 662 are roughly equal to each other.

On the other hand, among the three connectors 631 provided to the second connector section 63, in the connector 631A located on the +X side, there are disposed the (k+1)-th external connection terminal 632 through the $k_3$-th ($k+1 \le k_3 < n$) external connection terminal 632. Further, in the connector 631A, the (k+1)-th external connection terminal 632 is disposed at the +X side end part, and the $k_3$-th external connection terminal 632 is disposed at the −X side end part.

Among the three connectors 631 provided to the second connector section 63, in the connector 631B located in the central part in the X direction, there are disposed the ($k_3$+1)-th external connection terminal 632 through the $k_4$-th ($k_3 < k_4 < n$) external connection terminal 632. Further, in the connector 631B, the ($k_3$+1)-th external connection terminal 632 is disposed at the +X side end part, and the $k_4$-th external connection terminal 632 is disposed at the −X side end part.

Among the three connectors 631 provided to the second connector section 63, in the connector 631C located on the −X side, there are disposed the ($k_4$+1)-th external connection terminal 632 through the n-th external connection terminal 632. Further, in the connector 631C, the ($k_4$+1)-th external connection terminal 632 is disposed at the +X side end part, and the n-th external connection terminal 632 is disposed at the −X side end part.

Therefore, in the second connector section 63, the "i ($k+1 \le i \le n$)"-th external connection terminal 632 from the +X side corresponds to the i-th external connection terminal 632.

Further, to the i-th external connection terminal 632, there are connected the third interconnection 663 connected to the i-th first device-side terminal 531, and the fourth interconnection 664 connected to the i-th second device-side terminal 532.

Here, the third interconnection 663 and the fourth interconnection 664 disposed in the second connector section 63 are made roughly line-symmetric about the Y-central axis line $L_Y$ similarly to the device connection section 61. In other words, the wiring length from the first device-side terminal 531 to the external connection terminal 632 in the third interconnection 663 and the wiring length from the second device-side terminal 532 to the external connection terminal 622 in the fourth interconnection 664 are roughly equal to each other.

Here, among the first device-side terminals 531, it is preferable for the number (k) of the first device-side terminals 531 to be connected to the external connection terminals 622 of the first connector section 62, and the number (n−k) of the first device-side terminals 531 to be connected to the external connection terminals 632 of the second connection section 63 to satisfy the relationship of $|(n-k)-k|/n \le 0.2$.

In other words, it is preferable to adopt the wiring configuration in which the difference between the number (k) of the first device-side terminals 531 to be connected to the external connection terminals 622 and the number (n−k) of the first device-side terminals 531 to be connected to the external connection terminals 632 is equal to or lower than 20% of the total number (n) of the first device-side terminals 531. Further, it is more preferable that n is an even number, and k=n/2 is assumed.

Figure 10:
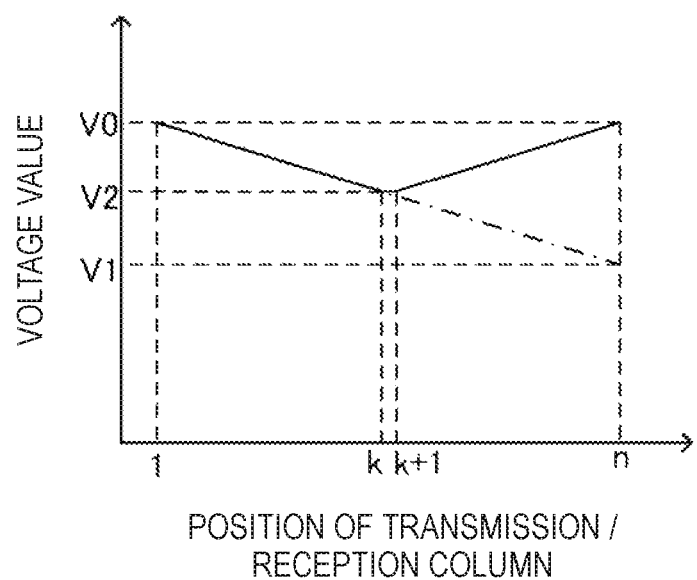
FIG. 10 is a diagram showing a voltage value of a drive voltage to be applied to each of transmission/reception columns of an ultrasonic device.

FIG. 10 is a diagram showing a voltage value of a drive voltage to be applied to each of the transmission/reception columns Ch. In FIG. 10, the dashed-dotted line represents the voltage value in the case of using the flexible board (related art example) having just one connector section with respect to the device connection section, and the solid line represents the voltage value in the present embodiment.

As shown in FIG. 10, in the past, the device-side terminals located close to the connector section are connected to the external connection terminals located on the device connection section side of the connector section, and the device-side terminals located farther from the connector section are connected to the external connection terminals located farther from the device connection section of the connector section. Therefore, as the device-side terminal is located farther from the connector section, the length of the interconnection also increases, and due to the influence of the voltage drop, the voltage value of the drive voltage applied to each of the transmission/reception columns Ch connected to the device-side terminals also drops.

In contrast, in the present embodiment, there are provided the first connector section 62 and the second connector section 63 as described above, and the interconnections 661, 662 are provided to the connector section 62, and the interconnections 663, 664 are provided to the connector section 63, wherein the numbers of the interconnections 661, 662, 663, and 664 are the same. Further, in the present embodiment, the first interconnections 661 and the third interconnections 663 are made roughly line-symmetric about an X-central axis line $L_X$ passing through the center of the ultrasonic device 5 and parallel to the Y direction, and the second interconnections 662 and the fourth interconnections 664 are made roughly line-symmetric about the X-central axis line $L_X$. Therefore, the first interconnection 661 connected to the i-th first device-side terminal 531, the second interconnection 662 connected to the i-th second device-side terminal 532, the third interconnection 663 connected to the (n−i+1)-th first device-side terminal 531, and the fourth interconnection 664 connected to the (n−i+1)-th second device-side terminal 532 become roughly the same in length, and as shown in FIG. 10, the influence of the voltage drop is suppressed.

2-2-3. Configuration of First Inflective Part 64 and Second Inflective Part 65

As shown in FIG. 8, the first inflective part 64 is disposed between the device connection section 61 and the first connector section 62, and links the first connector section 62 to the device connection section 61 in a bendable manner. Similarly, the second inflective part 65 is disposed between the device connection section 61 and the second connector section 63, and links the second connector section 63 to the device connection section 61 in a bendable manner.

The first inflective part 64 has the first slit 641 connected to the opening part 611 provided to the device connection section 61, and first linking parts 642 connected to the device connection section 61 and the first connector section 62 respectively on the ±Y sides of the first slit 641.

As shown in FIG. 8, the first slit 641 is an opening elongated along the Y direction (a direction crossing the direction from the device connection section 61 toward the first connector section 62), and includes the first negative-side end edge 612A, which is the end edge on the −X side of the first connection part 614 and the first bending part 615, and the second negative-side end edge 613A, which is the end edge on the −X side of the second connection part 617 and the second bending part 618 as a part of the opening edge on the +X side. In the present embodiment, the first negative-side end edge 612A and the second negative-side end edge 613A are located on a straight line along the Y direction. The opening edge opposed to the first negative-side end edge 612A and the second negative-side end edge 613A of the first slit 641 forms a first opposed edge 641A shaped like a straight line parallel to the Y direction.

Further, the end edge (a first slit end edge 641B) on the −Y side of the first slit 641 links the −Y side end parts of the first opposed edge 641A and the first negative-side end edge 612A to each other, and the end edge (a first slit end edge 641C) on the +Y side of the first slit 641 links the +Y side end parts of the first opposed edge 641A and the second negative-side end edge 613A to each other. The first slit end edge 641B is disposed at a position shifted from the first connection part 614 toward the −Y side as much as a dimension D1. Similarly, the first slit end edge 641C is disposed at a position shifted from the second connection part 617 toward the +Y side as much as the dimension D1.

Here, the dimension D1 is set to a dimension larger than a distance from the wiring board 53 to a first side 71A (see FIG. 11) of the first reinforcing plate 71 in the case of connecting the flexible board 6 to the ultrasonic device 5 supported by the first reinforcing plate 71 (see FIG. 11) described later.

The second inflective part 65 has the second slit 651 connected to the opening part 611 provided to the device connection section 61, and second linking parts 652 connected to the device connection section 61 and the second connector section 63 respectively on the ±Y sides of the second slit 651.

The second slit 651 has roughly the same configuration as that of the first slit 641, and is connected to the opening part 611, including the first positive-side end edge 612B and the second positive-side end edge 613B as a part of the opening edge on the −X side. The opening edge opposed to the first positive-side end edge 612B and the second positive-side end edge 613B of the second slit 651 forms a second opposed edge 651A shaped like a straight line parallel to the Y direction.

Further, the end edge (a second slit end edge 651B) on the −Y side of the second slit 651 links the −Y side end parts of the second opposed edge 651A and the first positive-side end edge 612B to each other, and the end edge (a second slit end edge 651C) on the +Y side of the second slit 651 links the +Y side end parts of the second opposed edge 651A and the second positive-side end edge 613B to each other. The second slit end edge 651B is disposed at a position shifted from the first connection part 614 toward the −Y side as much as the dimension D1, and the second slit end edge 651C is disposed at a position shifted from the second connection part 617 toward the +Y side as much as the dimension D1.

Incidentally, the first device-side terminals 531 to which the first connection part 614 is connected are disposed on the −Y side end part of the ultrasonic device 5, and the second device-side terminals 532 to which the second connection part 617 is connected are disposed on the +Y side end edge of the ultrasonic device 5. The fact that the first slit end edge 641B and the first connection part 614 are distant from each other as much as the dimension D1, and the first slit end edge 641C and the second connection part 617 are distant from each other as much as the dimension D1 means that the width dimension in the Y direction of the first slit 641 is larger than the width dimension in the Y direction of the ultrasonic device 5. Similarly, the width dimension in the Y direction of the second slit 651 is larger than the width dimension in the Y direction of the ultrasonic device 5.

Here, the dimension from the first negative-side end edge 612A to the first opposed edge 641A and the dimension from the second negative-side end edge 613A to the first opposed edge 641A are the same as each other, and are defined as a width dimension W1 in the X direction in the first slit 641. Further, the dimension from the first positive-side end edge 612B to the second opposed edge 651A and the dimension from the second positive-side end edge 613B to the second opposed edge 651A are the same as each other, and are defined as a width dimension W2 in the X direction in the second slit 651. In the present embodiment, the width dimension W1 of the first slit 641 and the width dimension W2 of the second slit 651 are different from each other, and satisfy W1<W2.

2-3. Configuration of First Reinforcing Plate 71 and Second Reinforcing Plate 72

2-3-1. Configuration of First Reinforcing Plate 71

Figure 11:
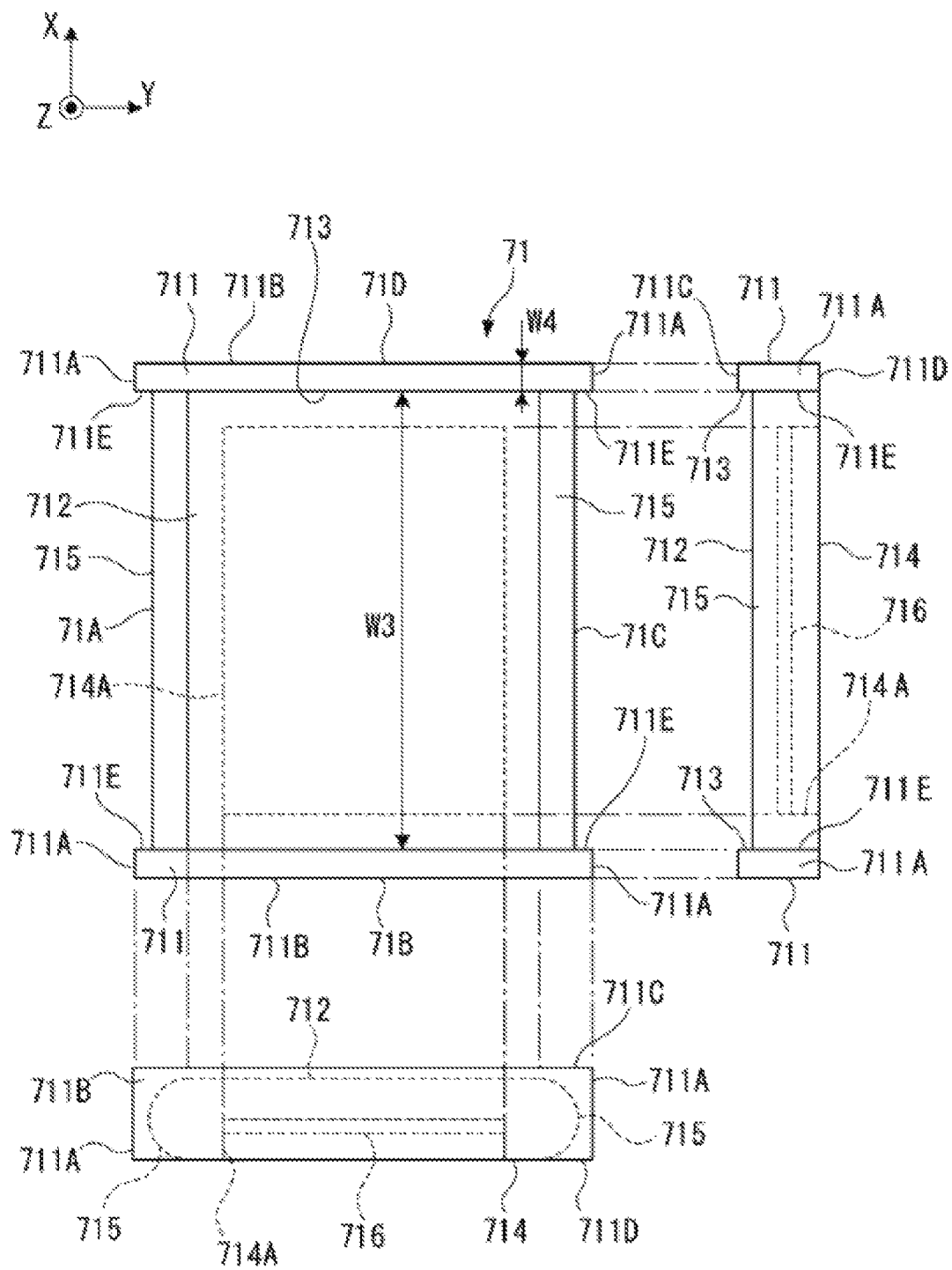
FIG. 11 is a plan view, a front view, and a side view of a first reinforcing plate of the embodiment.

FIG. 11 is a plan view, a front view, and a side view of a first reinforcing plate 71.

The first reinforcing plate 71 supports the ultrasonic device 5, and is fixed to the housing 21. Further, the first reinforcing plate 71 is formed of a resin material in order to prevent short circuit of the interconnections of the flexible board 6 when the first reinforcing plate 71 has contact with the flexible board 6 connected to the ultrasonic device 5.

As shown in FIG. 11, the first reinforcing plate 71 has, for example, a roughly rectangular shape in a plan view viewed from the substrate thickness direction, and is provided with a first side 71A (−Y side) and a third side 71C (+Y side) parallel to the X direction, and a second side 71B (−X side) and a fourth side 71D (+X side) parallel to the Y direction.

The second side 71B and the fourth side 71D each form a side parallel to the extending direction of the first bending part 615 and the second bending part 618 in the case of fixing the ultrasonic device 5 to the first reinforcing plate 71 and connecting the flexible board 6 to the ultrasonic device 5. The first side 71A and the third side 71C each form a side crossing the extending direction of the first bending part 615 and the second bending part 618 in the case of fixing the ultrasonic device 5 to the first reinforcing plate 71 and connecting the flexible board 6 to the ultrasonic device 5.

The first reinforcing plate 71 is provided with positioning blocks 711 along the second side 71B and the fourth side 71D, respectively. Specifically, there are disposed the positioning block 711 located in an area from a corner part between the first side 71A and the second side 71B through a corner part between the second side 71B and the third side 71C, and the positioning block 711 located in an area from a corner part between the third side 71C and the fourth side 71D through a corner part between the fourth side 71D and the first side 71A. These positioning blocks 711 each correspond to reference corner parts. For example, the positioning block 711 disposed along the second side 71B includes the reference corner part with respect to the corner part between the first side 71A and the second side 71B, and the reference corner part with respect to the corner part between the third side 71C and the second side 71B.

Each of the positioning blocks 711 is provided with first reference surfaces 711A parallel to the X direction, a second reference surface 711B parallel to the Y direction, and a third reference surface 711C and a fourth reference surface 711D crossing the first reference surfaces 711A and the second reference surface 711B.

Specifically, the first reference surfaces 711A are ±Y side end surfaces of the positioning block 711, and are planes parallel to the X-Z plane.

The second reference surface 711B is a −X side end surface in the positioning block 711 located on the second side 71B side, and a +X side end surface in the positioning block 711 located on the fourth side 71D side, and is a plane parallel to the Y-Z plane.

The third reference surface 711C is a +Z side end surface of each of the positioning blocks 711, and has contact with the housing 21. The third reference surface 711C is located on the +Z side with respect to the surface (a fixation surface 712) on the +Z side of the central part of the first reinforcing plate 71. Thus, a step 713 is disposed between the third reference surface 711C and the fixation surface 712, and due to the step 713, the ±X side end surfaces of the ultrasonic device 5 are positioned. Here, it is preferable for the height dimension (the dimension in the Z direction) of the step 713 to be equal to or larger than at least the thickness dimension of the flexible board 6. It should be noted that the fixation surface 712 is a surface for supporting the ultrasonic device 5, and corresponds to a support part.

The fourth reference surface 711D is a surface forming a reverse surface with respect to the third reference surface 711C, and when housing the ultrasonic device unit 4 in the housing 21, the second reinforcing plate 72 described later is mounted on the fourth reference surface 711D.

It should be noted that in the present embodiment, the fourth reference surface 711D is disposed in the same plane as the reverse surface 714 as shown in FIG. 11.

Further, the width dimension W4 in the X direction of the positioning block 711 is smaller than the width dimension W1 of the first slit 641 and the width dimension W2 of the second slit 651 (see FIG. 8).

Further, in each of the positioning blocks 711, a surface (a surface on the opposite side to the second reference surface 711B) crossing the first side 71A and the third side 71C forms a guide surface 711E. The guide surface 711E is a surface parallel to the Y-Z plane, and has contact with the end edges 612A, 612B, 613A, and 613B when bending the first bending part 615 and the second bending part 618 of the flexible board 6 along the bending guide part 715.

Further, on the ±Y sides of the fixation surface of the first reinforcing plate 71, there are disposed the bending guide parts 715 along the first side 71A and the third side 71C, respectively. The Y-Z cross-section of the bending guide part 715 has an arc-like shape protruding in a direction of getting away from the fixation surface 712, and continuous with the fixation surface 712 and the reverse surface 714.

Here, the tip of the protrusion of the bending guide part 715 is located on the fixation surface 712 side of the first reference surface 711A. Specifically, the first reference surfaces 711A located on the both end sides of the first side 71A are located at a position shifted from the −Y side end part of the bending guide part 715 extending along the first side 71A toward the −Y side as much as an amount at least equal to or larger than the thickness of the flexible board 6. Further, the first reference surfaces 711A located on the both end sides of the third side 71C are located at a position shifted from the +Y side end part of the bending guide part 715 extending along the third side 71C toward the +Y side as much as an amount at least equal to or larger than the thickness of the flexible board 6.

Further, the distance along the X direction between a pair of guide surfaces 711E opposed to each other across the first side 71A is roughly the same as the width dimension W3 in the X direction of the first connection part 614 and the first bending part 615 of the flexible board 6.

Incidentally, the first reinforcing plate 71 is formed of the resin material as described above, and is therefore lower in strength compared to the case of being formed of, for example, metal. Therefore, in order to increase the substrate strength, the first reinforcing plate 71 is provided with a recessed part 714A disposed on the reverse surface 714, and a metal plate 716 is disposed in the recessed part 714A. The metal plate 716 is disposed on the bottom surface of the recessed part 714A, and does not protrude outward (the −Z side) from the reverse surface 714. Thus, even when bending the flexible board 6 on the reverse surface 714 side of the first reinforcing plate 71, the flexible board 6 and the metal plate 716 do not interfere with each other.

2-3-2. Configuration of Second Reinforcing Plate 72

As shown in FIG. 3 and FIG. 4, the second reinforcing plate 72 supports the second connector section 63.

Figure 12:
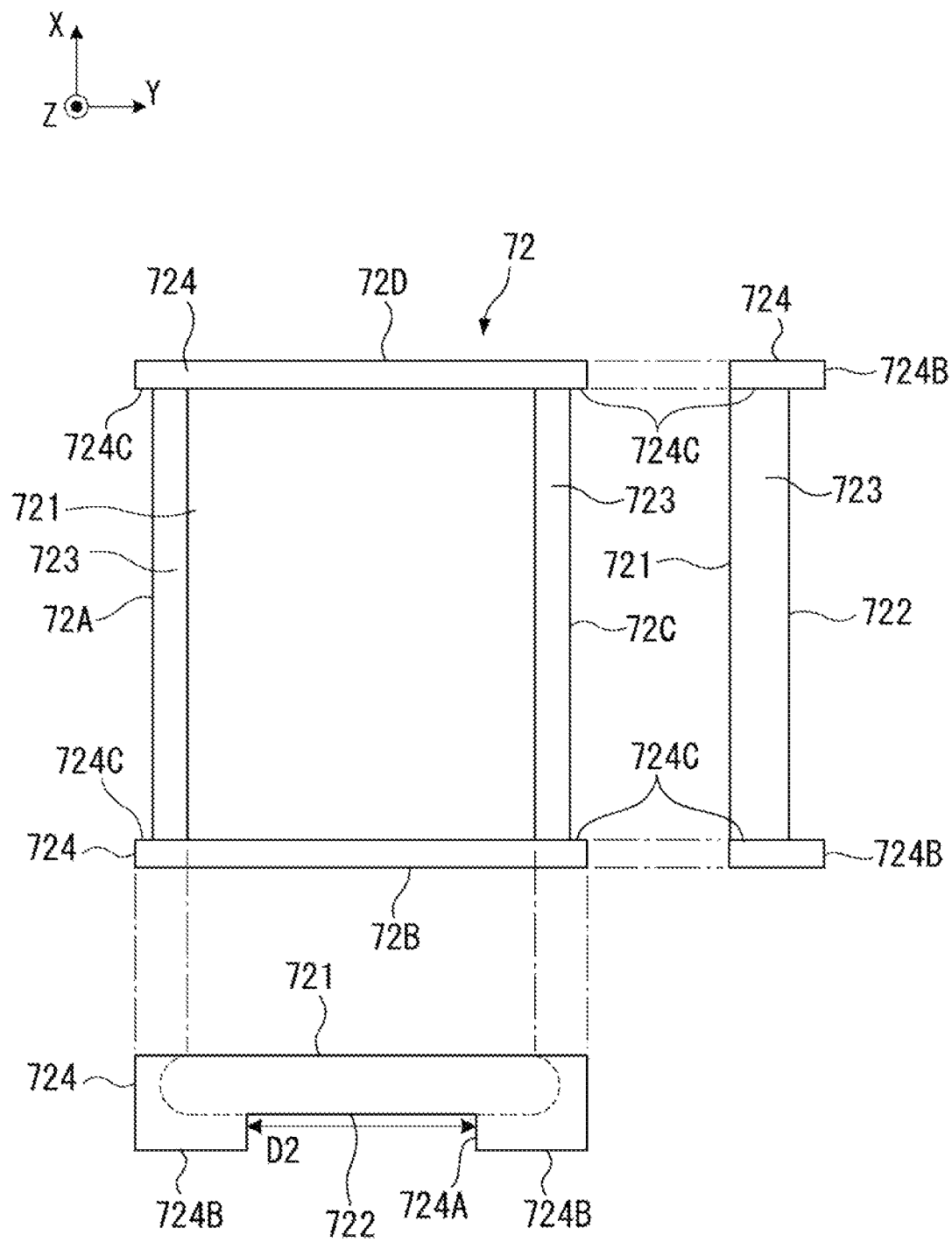
FIG. 12 is a plan view, a front view, and a side view of a second reinforcing plate of the embodiment.

FIG. 12 is a plan view, a front view, and a side view of the second reinforcing plate 72.

As shown in FIG. 12, the second reinforcing plate 72 has a roughly rectangular shape having a fifth side 72A, a sixth side 72B, a seventh side 72C, and an eighth side 72D in a planar view viewed from the plate thickness direction similarly to the first reinforcing plate 71.

The second reinforcing plate 72 is provided with a connector support surface 721 with which the central part (an area where the connectors 631 are disposed) of the second connector section 63 has contact, and a reverse surface 722 on the opposite side to the connector support surface 721. Further, the second reinforcing plate 72 is provided with second bending guide parts 723 each curved to have an arc-like shape disposed respectively in the fifth side 72A and the seventh side 72C extending along the X direction similarly to the first reinforcing plate 71.

Further, the second reinforcing plate 72 is provided with second positioning blocks 724 respectively disposed along the sixth side 72B and the eighth side 72D located on the ±X sides similarly to the first reinforcing plate 71.

The second positioning blocks 724 are each provided with a recessed part 724A on a surface on the opposite side to the connector support surface 721. The recessed part 724A forms a configuration space for the first inflective part 64 and the second inflective part 65 of the flexible board 6. Specifically, the width dimension D2 in the Y direction of the recessed part 724A of the second positioning block 724 located on the −X side is equal to or larger than the dimension D3 (see FIG. 8) from the −Y side end edge of the first inflective part 64 to the first slit end edge 641B, and the dimension D4 (see FIG. 8) from the +Y side end edge of the first inflective part 64 to the first slit end edge 641C, and it is preferable to fulfill D2=D3=D4.

Further, although not shown in the drawings, the width dimension in the Y direction of the recessed part 724A of the second positioning block 724 located on the +X side is equal to or larger than the dimension D6 (see FIG. 8) from the −Y side end edge of the second inflective part 65 to the second slit end edge 651B, and the dimension D7 (see FIG. 8) from the +Y side end edge of the second inflective part 65 to the second slit end edge 651C, and is preferably equal to the dimensions D6 and D7.

That is, by making the width dimension in the Y direction of the recessed part 724A equal to the width dimension in the Y direction of the first linking part 642 and the second linking part 652, it is possible to support the end edges (a first outer edge part 6A, a second outer edge part 6B, the first slit end edges 641B, 641C, and the second slit end edges 651B, 651C) on the ±Y sides of the first linking part 642 and the second linking part 652 with the inner periphery side surfaces of the recessed part 724A.

Further, on a surface on the opposite side to the connector support surface 721 of the second positioning block 724, there are disposed mount surfaces 724B across the recessed part 724A from each other. The mount surfaces 724B are mounted on the fourth reference surface 711D when storing the second reinforcing plate 72 in the housing 21.

In the present embodiment, the mount surfaces 724B are located on the −Z side (+Z side when stored in the housing 21) of the reverse surface 722. Thus, when mounting the mount surfaces 724B on the fourth reference surface 711D, between the reverse surface 714 of the first reinforcing plate 71 and the reverse surface 722 of the second reinforcing plate 72, there is formed a space at least equal to or larger than the configuration space S for the flexible board 6 that is folded multiple times and the connectors 621 of the first connector section 62.

The surface on the fifth side 72A side and on the seventh side 72C side of each of the second positioning blocks 724 forms a second guide surface 724C for guiding the second opposed edge 651A of the second slit 651 of the flexible board 6, and an outer peripheral edge on the −X side of the flexible board 6.

2-4. Configuration of Housing 21

As shown in FIG. 2, the housing 21 is provided with a storage part 211 and a lid part 212.

As shown in FIG. 3 and FIG. 4, the storage part 211 is a vessel-like member for storing the ultrasonic device unit 4, and has a sensor window 211B in a bottom part 211A, wherein the acoustic lens 54 of the ultrasonic device 5 is exposed to the outside from the sensor window 211B.

Further, in the bottom part 211A of the storage part 211, there is disposed a device installation part 213 (a unit holding part) so as to surround the sensor window 211B. The device installation part 213 is formed to have a frame-like shape rising from the bottom part 211A so that the four corners of the first reinforcing plate 71 are fitted into the device installation part 213.

2-5. Storage of Ultrasonic Device Unit 4 into Housing 21

In such an ultrasonic probe 2 as described above, firstly, the ultrasonic device 5 is fixed to the fixation surface 712 of the first reinforcing plate 71.

Then, the first connection part 614 of the flexible board 6 is connected to the −X side of the wiring board 53 of the ultrasonic device 5. Thus, the connection terminals of the first connection part 614 and the first device-side terminals 531 are electrically connected to each other, respectively. Further, the second connection part 617 is connected to the +X side of the wiring board 53 of the ultrasonic device 5. Thus, the connection terminals of the second connection part 617 and the second device-side terminals 532 are electrically connected to each other, respectively.

On this occasion, the first negative-side end edge 612A of the flexible board 6 is made to have contact with (be guided by) the guide surface 711E located on the −X side of the first side 71A, and the first positive-side end edge 612B is made to have contact with (be guided by) the guide surface 711E located on the +X side of the first side 71A. Further, the second negative-side end edge 613A of the flexible board 6 is made to have contact with (be guided by) the guide surface 711E located on the −X side of the third side 71C, and the second positive-side end edge 613B is made to have contact with (be guided by) the guide surface 711E located on the +X side of the third side 71C.

Figure 13:
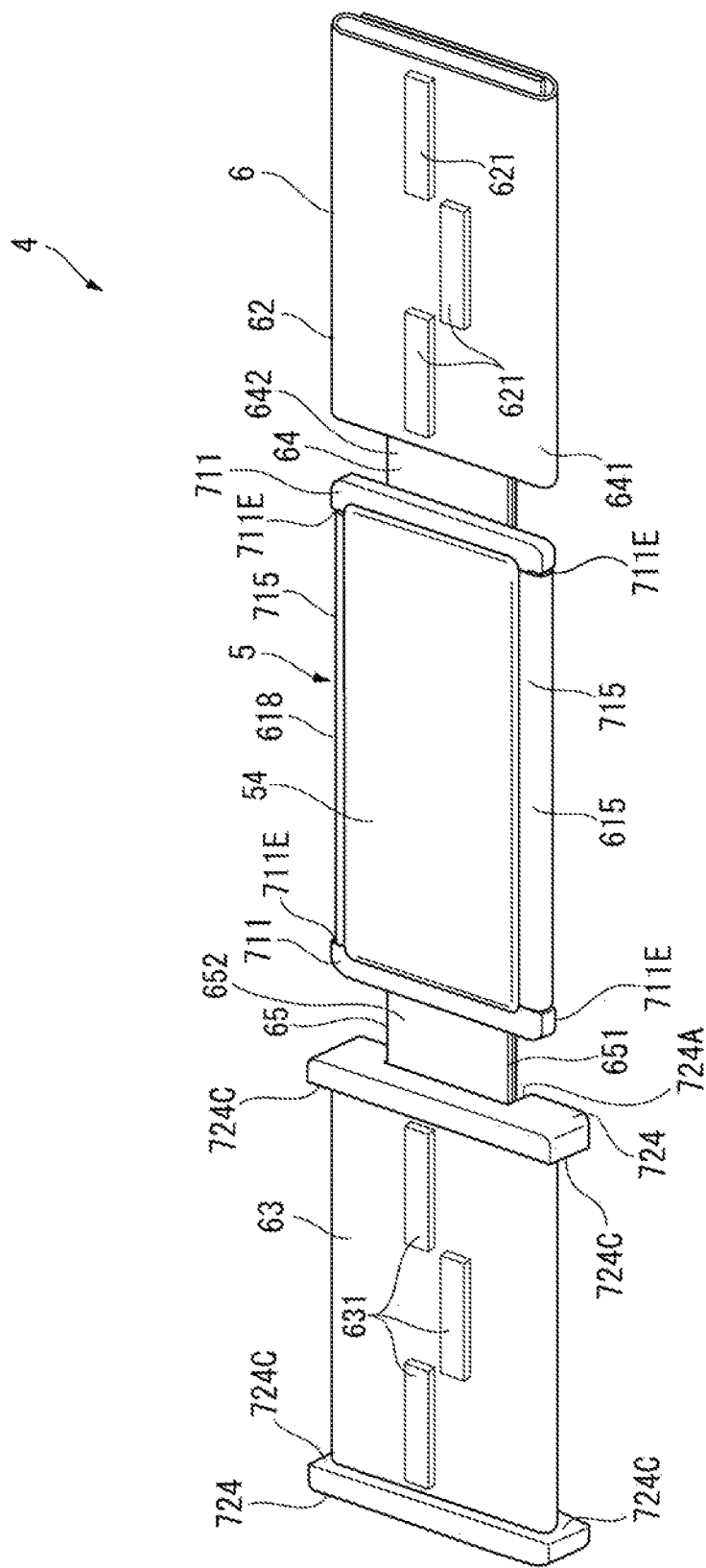
FIG. 13 is a perspective view of the case in which the flexible board is curved along an X direction in the embodiment.

FIG. 13 is a perspective view of the case in which the flexible board 6 is curved along the X direction in the present embodiment.

Subsequently, the flexible board 6 is curved in a first bending area Ar3 (see FIG. 8) including the first bending part 615 parallel to the X direction to fold back the end edge on the −Y side of the flexible board 6 toward the +Y side. Further, the flexible board 6 is curved in a second bending area Ar4 (see FIG. 8) including the second bending part 618 parallel to the X direction to fold back the end edge on the +Y side of the flexible board 6 toward the −Y side. It should be noted that either one of the first bending area Ar3 and the second bending area Ar4 can be folded back first.

Here, as shown in FIG. 13, the end edges (the first negative-side end edge 612A and the first positive-side end edge 612B) of the ±X sides of the first bending part 615 and the end edges (the second negative-side end edge 613A and the second positive-side end edge 613B) on the ±X sides of the second bending part 618 are guided by the guide surfaces 711E to be curved along the arcs of the bending guide parts 715.

Thus, in the flexible board 6, the first bending area Ar3 can be bent along (in parallel to the X direction) the first side 71A of the first reinforcing plate 71, and thus, the first device stacking part 616 is stacked on the reverse surface 714 side of the first reinforcing plate 71 so as to overlap the first reinforcing plate 71. Further, the second bending area Ar4 can be bent along (in parallel to the X direction) the third side 71C of the first reinforcing plate 71, and thus, the second device stacking part 619 is stacked on the reverse surface 714 side of the first reinforcing plate 71 so as to overlap the first reinforcing plate 71.

Similarly, in each of the first connector section 62, the first inflective part 64 and the second inflective part 65, an area located on the −Y side of the first bending area Ar3 is made to overlap a central area Ar5. Further, in each of the first connector section 62, the first inflective part 64 and the second inflective part 65, an area located on the +Y side of the second bending area Ar4 is made to overlap the central area Ar5.

Further, the first bending area Ar3 and the second bending area Ar4 of the second connector section 63 are guided by the second guide surfaces 724C to be curved along the second bending guide parts 723 of the second reinforcing plate 72, and thus, an area located on the −Y side of the first bending area Ar3 of the second connector section 63 and an area located on the +Y side of the second bending area Ar4 are made to overlap the reverse surface of the second reinforcing plate 72.

As described above, when curving the flexible board 6, the first slit end edges 641B, 641C of the first slit 641 and the second slit end edges 651B, 651C of the second slit 651 move to the positions to be overlapped with the central area Ar5. Therefore, even in the case in which the flexible board 6 is folded back in the first bending area Ar3 and the second bending area Ar4 to be deformed to have a roughly cylindrical shape, in each of the first inflective part 64 and the second inflective part 65, there is formed a shape in which the two first linking parts 642 (the two second linking parts 652 in the second inflective part 65) overlap each other only on the reverse surface 714 side of the first reinforcing plate 71. In other words, the first inflective part 64 and the second inflective part 65 do not form a cylindrical shape, but are easily bent toward the reverse surface 714 side of the first reinforcing plate 71.

Further, in the present embodiment, the width dimension W1 in the X direction of the first slit 641 in the first inflective part 64 is smaller than the width dimension W2 in the X direction of the second slit 651 in the second inflective part 65. Therefore, when bending the first inflective part 64 and second inflective part 65, the first inflective part 64 is bent first, and then the first connector section 62 is overlapped with the first reinforcing plate 71. Here, since the X-width dimension of the first connector section 62 is smaller than the X-width dimension of the first reinforcing plate 71, the first connector section 62 does not project toward the second inflective part 65, and does not hinder bending of the second inflective part 65.

Further, by bending the first inflective part 64 toward the reverse surface 714 side of the first reinforcing plate 71, the connectors 621 in the first connector section 62 project toward the −Z side.

Then, the first reinforcing plate 71 is fixed to the storage part 211 of the housing 21.

Specifically, as shown in FIG. 3 and FIG. 4, the first reference surfaces 711A and the second reference surfaces 711B of the positioning blocks 711 provided to the first reinforcing plate 71 are made to have contact with, and then fitted into, the device installation part 213 provided to the housing 21. Thus, the third reference surfaces 711C of the first reinforcing plate 71 have contact with the bottom part 211A of the housing 21, and the acoustic lens 54 of the ultrasonic device 5 projects from the sensor window 211B.

Further, on this occasion, each of the connectors 621 in the first connector section 62 is exposed on the opposite side to the bottom part 211A of the storage part 211. Then, the terminals disposed on the tip of the cable 3 are connected to the connectors 621.

Figure 14:
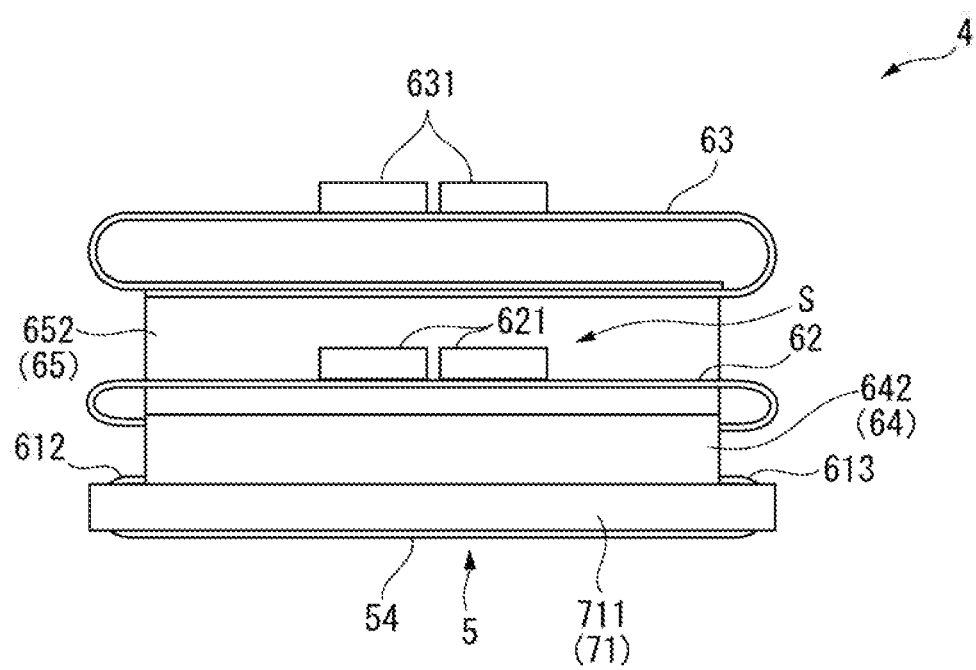
FIG. 14 is a side view of an ultrasonic device unit according to the embodiment viewed from a first inflective part side.
Figure 15:
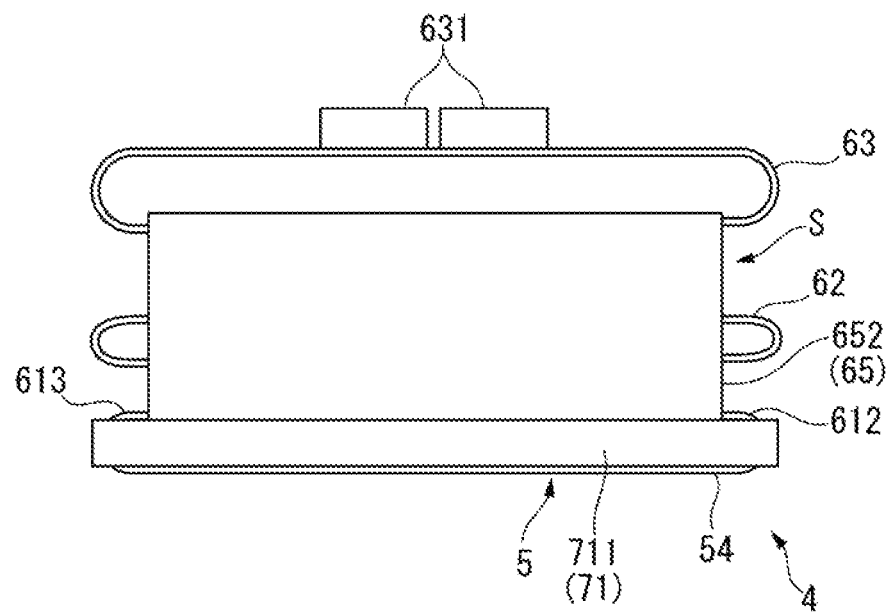
FIG. 15 is a side view of the ultrasonic device unit according to the embodiment viewed from a second inflective part side.

FIG. 14 is a side view of the ultrasonic device unit 4 housed in the housing 21 viewed from the first inflective part 64 side, and FIG. 15 is a side view viewed from the second inflective part 65 side. It should be noted that the illustration of the second reinforcing plate 72 is omitted in FIG. 14 and FIG. 15.

Subsequently, the second inflective part 65 is bent to overlap the second reinforcing plate 72 which supports the second connector section 63 with the first reinforcing plate 71. Thus, the mount surfaces 724B of the second positioning blocks 724 of the second reinforcing plate 72 are mounted on the fourth reference surfaces 711D of the positioning blocks 711 of the first reinforcing plate 71.

On this occasion, since the width dimension W2 of the second slit 651 in the second inflective part 65 satisfies W2>W1, the second connector section 63 does not interfere with the first connector section 62, and the first inflective part 64 and the second inflective part 65 do not project outside as shown in FIG. 14 and FIG. 15, and therefore, miniaturization of the flexible board 6 can be advanced.

Further, when mounting the mount surfaces 724B of the second reinforcing plate 72 on the fourth reference surfaces 711D of the first reinforcing plate 71, the configuration space S for disposing the flexible board 6 and the first connector section 62 is formed between the reverse surface 714 of the first reinforcing plate 71 and the reverse surface 722 of the second reinforcing plate 72. In the configuration space S, there are disposed the first device stacking part 616, the second device stacking part 619, the first connector section 62 bent to be triply overlapped, the second connector section 63 bent toward the reverse surface 722 side of the second reinforcing plate 72 to be doubly overlapped, the connectors in the first connector section 62, and the terminals of the cable 3 to be connected to the connectors (the illustration of the cable 3 is omitted in FIG. 2 and FIG. 3).

Further, since the connectors 631 of the second connector section 63 supported by the second reinforcing plate 72 are exposed on the −Z side, the terminals provided to the tip of the cable 3 are connected to the connectors 631. Subsequently, the lid part 212 is fixed to the storage part 211, and the space between the sensor window 211B and the acoustic lens 54 is sealed with a resin material such as silicone resin, and thus, the ultrasonic probe 2 is assembled.

3. Functions and Advantages of Embodiment

The ultrasonic device unit 4 according to the present embodiment is provided with the ultrasonic device 5, the flexible board 6 connected to the ultrasonic device 5, and the first reinforcing plate 71 for supporting the ultrasonic device 5. The flexible board 6 is provided with the first connection part 614 and the second connection part 617 to be connected to the ultrasonic device 5, and the first bending part 615 and the second bending part 618 extending respectively from the first connection part 614 and the second connection part 617. Further, the first reinforcing plate 71 has the bending guide parts 715 respectively opposed to the first bending part 615 and the second bending part 618 in the case of fixing the ultrasonic device 5 to the fixation surface 712, and connecting the flexible board 6 to the ultrasonic device 5. Further, the first reinforcing plate 71 is provided with the guide surfaces 711E for guiding the end edges (the first negative-side end edge 612A, the first positive-side end edge 612B, the second negative-side end edge 613A, and the second positive-side end edge 613B) of the first bending part 615 and the second bending part 618 on the both sides (±X sides) of the bending guide parts 715.

Therefore, when connecting the flexible board 6 to the ultrasonic device 5, and when curving the flexible board 6 in the first bending area Ar3 and the second bending area Ar4, it is possible for the end edges of the first bending part 615 and the second bending part 618 to have contact with, and be guided by, the guide surfaces 711E. Thus, it is possible to make the X-Y direction of the flexible board 6 and the X-Y direction of the ultrasonic device 5 and the first reinforcing plate 71 coincide with each other, and the tilt of the flexible board 6 can be suppressed, and the flexible board 6 can be disposed in an appropriate position.

Further, by curving the first bending part 615 and the second bending part 618 along the bending guide parts 715 each having the circular arc curved surface, breaking of the interconnections 661, 662, 663, and 664 disposed on the first bending part 615 and the second bending part 618 can be prevented. In addition, by curving the first bending part 615 and the second bending part 618 along the bending guide part 715, it is possible to bend the first bending area Ar3 and the second bending area Ar4 of the flexible board 6 along the first side 71A and the third side 71C of the first reinforcing plate 71 without tilting the flexible board 6.

According to the above, it is possible to prevent the disadvantage that a part of the flexible board 6 fails to overlap the first reinforcing plate 71, but projects from the outer edge (the first side 71A, the second side 71B, the third side 71C, and the fourth side 71D) of the first reinforcing plate 71 in the planar view, and thus, it is possible to achieve the miniaturization of the ultrasonic device unit 4.

Thus, the miniaturization in the ultrasonic probe 2 incorporating the ultrasonic device unit 4 and the ultrasonic measurement apparatus 1 can also be advanced.

In the ultrasonic device unit 4 according to the present embodiment, the first reference surfaces 711A located on the both end sides of the first side 71A are located at a position shifted from the −Y side end part of the bending guide part 715 extending along the first side 71A toward the −Y side as much as an amount at least equal to or larger than the thickness of the flexible board 6. Further, the first reference surfaces 711A located on the both end sides of the third side 71C are located at a position shifted from the +Y side end part of the bending guide part 715 extending along the third side 71C toward the +Y side as much as an amount at least equal to or larger than the thickness of the flexible board 6. In other words, in the Y direction, the end part (the first reference surface 711A) of the guide surface 711E projects from the projecting tip of the bending guide part 715 as much as a dimension equal to or larger than the thickness of the flexible board 6.

Therefore, when curving the first bending part 615 and the second bending part 618 along the bending guide parts 715, the first bending part 615 and the second bending part 618 always have contact with the guide surfaces 711E. Thus, it is possible to appropriately curve to bend the flexible board 6 in the first bending area Ar3 and the second bending area Ar4. Further, when fitting the ultrasonic device unit 4 into the device installation part 213 of the housing 21, the flexible board 6 does not interfere with the housing 21, and thus, damages or the like of the flexible board 6 can also be prevented.

In the present embodiment, the positioning blocks 711 are disposed throughout the area from the crossing position between the first side 71A and the second side 71B to the crossing position between the second side 71B and the third side 71C, and throughout the area from the crossing position between the third side 71C and the fourth side 71D to the crossing position between the fourth side 71D and the first side 71A, respectively. In other words, the positioning blocks 711 are located at each of the four corners parts of the first reinforcing plate 71.

Therefore, when storing the ultrasonic device unit 4 in the housing 21, it is possible to make the first reference surfaces 711A and the second reference surfaces 711B of these positioning blocks 711 have contact with the wall surfaces of the device installation part 213 provided to the housing 21 to thereby achieve the positioning. Therefore, it is possible to fix the ultrasonic device unit 4 at an appropriate position with respect to the ultrasonic probe 2.

In the present embodiment, the flexible board 6 is provided with the first slit 641 including the first negative-side end edge 612A of the first bending part 615, the second negative-side end edge 613A of the second bending part 618, and the first opposed edge 641A, and the second slit 651 including the first positive-side end edge 612B of the first bending part 615, the second positive-side end edge 613B of the second bending part 618, and the second opposed edge 651A. Further, the width dimension W1 in the X direction of the first slit 641 and the width dimension W2 in the X direction of the second slit 651 are each larger than the width dimension in the X direction of the positioning block 711.

Therefore, in the case in which the end edges (the first negative-side end edge 612A, the first positive-side end edge 612B, the second negative-side end edge 613A, and the second positive-side end edge 613B) of the first bending part 615 and the second bending part 618 is made to be guided by (have contact with) the guide surfaces 711E, the positioning blocks 711 are inserted through the first slit 641 and the second slit 651. Therefore, the interference between the flexible board 6 and the positioning blocks 711 is prevented, and it is possible to prevent the disadvantage that, for example, the flexible board 6 covers the positioning blocks 711 to increase the size of the ultrasonic device unit 4.

In the present embodiment, the first reinforcing plate 71 is formed of a resin material. Thus, it is possible to prevent the short circuit of the interconnections 661, 662, 663, and 664 when installing the flexible board 6. Further, the first reinforcing plate 71 is provided with the recessed part 714A on the reverse surface 714 on the opposite side to the fixation surface 712 to which the ultrasonic device 5 is fixed, and the metal plate 716 is disposed in the recessed part 714A. Thus, it is possible to increase the strength of the first reinforcing plate 71 by the metal plate 716 even in the case of forming the first reinforcing plate 71 from the resin material.

Modified Examples

It should be noted that the invention is not limited to the embodiment and the modified examples described above, but includes modifications and improvements within a range in which the advantages of the invention can be achieved, and configurations which can be obtained by arbitrary combinations of the embodiment and modified examples, and so on.

In the embodiment described above, there is assumed the configuration in which the first reinforcing plate 71 is provided with the positioning blocks 711 throughout the areas around the second side 71B and the fourth side 71D, but it is also possible to adopt a configuration in which, for example, the reference corner parts each having a block shape provided with the first reference surface 711A and the second reference surface 711B are disposed at the respective four corners, namely the both ends of the second side 71B and the both ends of the fourth side 71D. Further, in such a configuration, it is sufficient to adapt a configuration in which the positioning blocks are disposed at either three of the four corners.

In the present embodiment, it is assumed that the width dimension in the X direction of the first slit 641 and the second slit 651 is larger than the width dimension in the X direction of the positioning blocks 711, but this is not a limitation. For example, it is also possible for the width dimension in the X direction of the first slit 641 and the second slit 651 to be smaller than the width dimension in the X direction of the positioning blocks 711. It should be noted that in the case of curving the flexible board 6 in the first bending area Ar3 and the second bending area Ar4, a part of the first connector section 62 and the second connector section 63 covers the area from the third reference surface 711C through the fourth reference surface 711D of the positioning block 711. Therefore, when bending the flexible board 6 in the first inflective part 64 and the second inflective part 65, it is necessary to pull out the first connector section 62 and the second connector section 63 covering the third reference surface 711C described above toward the X direction, and bending the flexible board 6 is accompanied by a complicated operation.

In this case, it is sufficient to form a tilted surface or a curved surface throughout an area from the third reference surface 711C to the second reference surface 711B of each of the positioning blocks 711. Thus, it is possible to easily pull out the first connector section 62 and the second connector section 63 covering the third reference surface 711C when bending the flexible board 6 in the first inflective part 64 and the second inflective part 65.

In the embodiment described above, there is adopted the configuration in which the recessed part 714A is provided to the reverse surface 714 of the first reinforcing plate 71, and the metal plate 716 is provided to the recessed part 714A, but this is not a limitation.

For example, it is possible to adopt a configuration in which, for example, the metal plate 716 is embedded inside the first reinforcing plate 71 without providing the recessed part 714A to the first reinforcing plate 71.

In the embodiment described above, there is shown the configuration in which the first reference surfaces 711A and the second reference surfaces 711B of the positioning blocks 711 are made to have contact with the device installation part 213 of the housing 21 to thereby achieve the positioning, but this is not a limitation. It is also possible to adopt a configuration in which, for example, the positioning blocks 711 are provided with a plurality of hole parts, and the housing 21 is provided with pins which can be fitted into the hole parts described above.

In the embodiment described above, there is shown the example in which the end parts of the guide surfaces 711E projects from the bending guide parts 715 in the Y direction, but it is also possible that, for example, the end part on the +Y side of the guide surface 711E and the +Y end part of the bending guide part 715 are located at the same position, and the end part on the −Y side of the guide surface 711E and the −Y end part of the bending guide part 715 are located at the same position.

In the embodiment described above, there is shown the example in which the ultrasonic device 5 transmits the ultrasonic wave from the substrate opening part 511A, and receives the ultrasonic wave entering the substrate opening part 511A. In contrast, it is also possible to adopt a configuration in which the sealing plate 52 is disposed on the substrate opening part 511A side, and the ultrasonic wave is output to the opposite side to the substrate opening part 511A.

Further, the transmission/reception column Ch provided with a plurality of ultrasonic transducers Tr is illustrated as the vibrator element provided to the ultrasonic device 5, but this example is not a limitation. For example, it is also possible that each of the ultrasonic transducers Tr can also be configured as a vibrator element.

Further, there is shown an example of the ultrasonic transducer Tr in which the ultrasonic wave is transmitted by vibrating the support film 512 with the piezoelectric element 513, and the ultrasonic wave is received by converting the vibration of the support film 512 into an electric signal with the piezoelectric element 513, but this example is not a limitation. For example, it is also possible to adopt a configuration in which the ultrasonic wave is transmitted and received by vibrating a bulk-type piezoelectric body, and further, it is also possible to adopt a configuration in which electrodes opposed to each other are provided to a pair of film members, and a cyclic drive voltage is applied between the electrodes to thereby vibrate the film members using electrostatic force.

In the embodiment described above, the ultrasonic measurement apparatus 1 taking an organ in a living body as the measurement object is illustrated as the ultrasonic apparatus, but this is not a limitation. For example, the configurations of the embodiment and the modified examples described above can be applied to a measurement apparatus taking a variety of types of structures as the measurement object, and performing detection of defects of the structures and inspections of aging of the structures. Further, the same applies to a measurement apparatus taking, for example, a semiconductor package or a wafer as the measurement object, and detecting the defects of the measurement object.

Besides the above, specific structures to be adopted when implementing the invention can be configured by arbitrarily combining the embodiment and the modified examples described above with each other, or can arbitrarily be replaced with other structures and so on within the range in which the advantages of the invention can be achieved.

The entire disclosure of Japanese Patent Application No. 2017-055814 filed Mar. 22, 2017 is expressly incorporated by reference herein.

What is claimed is:

1. An ultrasonic assembly comprising: three directions orthogonal to each other being defined as an X-direction, a Y-direction, and a Z-direction;
an ultrasonic device, the ultrasonic device having:
  a substrate in which a plurality of ultrasonic elements are formed, the substrate being rectangular-shaped and having a plane along the X-direction and the Y-direction; a wiring board overlapped with the substrate in the Z-direction, the wiring board being rectangular-shaped and having a plane along the X-direction and the Y-direction; and a terminal disposed on a first surface of the wiring board;
a reinforcing member, the reinforcing member being configured with:
  a support plate having a second surface and a third surface outwardly opposite to each other;
  a ledge provided at an edge of the support plate, the wiring board of the ultrasonic device being disposed on the support plate, the first surface of the wiring board facing the second surface of the support plate; and a guide path surface located at a side of the support plate including an area adjacent to a border between the support plate and the ledge; and a flexible printed wiring board disposed to face the third surface of the support plate of the reinforcing member, the flexible printed wiring board being overlapped with the ultrasonic device and the reinforcing member in the Z-direction, the flexible printed wiring board having:
    an end flexible board traveling on the guide path surface toward the first surface of the wiring board of the ultrasonic device, the end flexible board being connected to the terminal of the wiring board of the ultrasonic device; and
    a plurality of external connection terminals, wherein the flexible printed wiring board is configured to be folded a plurality of times, and first external connection terminals of the plurality of external connection terminals are overlapped with second external connection terminals of the plurality of external connection terminals in the Z-direction when the flexible printed wiring board is folded the plurality of times.

2. The ultrasonic assembly according to claim 1,
wherein the guide path surface of the reinforcing member starts from a position on the third surface of the support plate and ends at a position on the second surface of the support plate,
and the guide path surface is curved.

3. The ultrasonic assembly according to claim 1,
wherein the ledge of the support plate of the reinforcing member has a first plane and a second plane, and
the first plane is along the X-direction and the Z-direction, and the second plane is along the Y-direction and the Z-direction.

4. The ultrasonic assembly according to claim 3,
wherein the flexible printed wiring board has a slit that is located next to the ledge of the support plate of the reinforcing member when the flexible printed wiring board is overlapped with the reinforcing member, and
a width along the X-direction of the slit is equal to or larger than a width along the X-direction of the first plane of the ledge of the support plate of the reinforcing member.

5. The ultrasonic assembly according to claim 1,
wherein the reinforcing member is formed of a resin material, and a recess is formed in the third surface of the support plate, and a metal plate is disposed in the recess.

6. An ultrasonic apparatus comprising: three directions orthogonal to each other being defined as an X-direction, a Y-direction, and a Z-direction;
an ultrasonic assembly, the ultrasonic assembly including:
an ultrasonic device, the ultrasonic device having:
a substrate in which a plurality of ultrasonic elements are formed, the substrate being rectangular-shaped and having a plane along the X-direction and the Y-direction; a wiring board overlapped with the substrate in the Z-direction, the wiring board being rectangular-shaped and having a plane along the X-direction and the Y-direction; and
a terminal disposed on a first surface of the wiring board;
a reinforcing member, the reinforcing member being configured with:
a support plate having a second surface and a third surface outwardly opposite to each other;
a ledge provided at an edge of the support plate, the wiring board of the ultrasonic device being disposed on the support plate, the first surface of the wiring board facing the second surface of the support plate; and a guide path surface located at a side of the support plate including an area adjacent to a border between the support plate and the ledge; and a flexible printed wiring board disposed to face the third surface of the support plate of the reinforcing member, the flexible printed wiring board being overlapped with the ultrasonic device and the reinforcing member in the Z-direction, the flexible printed wiring board having:
an end flexible board traveling on the guide path surface toward the first surface of the wiring board of the ultrasonic device, the end flexible board being connected to the terminal of the wiring board of the ultrasonic device; and a plurality of external connection terminals; a memory configured to store a program; and a processor configured to execute the program so as to control the ultrasonic assembly, wherein the flexible printed wiring board is configured to be folded a plurality of times, and first external connection terminals of the plurality of external connection terminals are overlapped with second external connection terminals of the plurality of external connection terminals in the Z-direction when the flexible printed wiring board is folded the plurality of times.

7. The ultrasonic apparatus according to claim 6,
wherein the guide path surface of the reinforcing member starts from a position on the third surface of the support plate and ends at a position on the second surface of the support plate,
and the guide path surface is curved.

8. The ultrasonic apparatus according to claim 6,
wherein the ledge of the support plate of the reinforcing member has a first plane and a second plane, and
the first plane is along the X-direction and the Z-direction, and the second plane is along the Y-direction and the Z-direction.

9. The ultrasonic apparatus according to claim 8,
wherein the flexible printed wiring board has a slit that is located next to the ledge of the support plate of the reinforcing member when the flexible printed wiring board is overlapped with the reinforcing member, and
a width along the X-direction of the slit is equal to or larger than a width along the X-direction of the first plane of the ledge of the support plate of the reinforcing member.

10. The ultrasonic apparatus according to claim 6,
wherein the reinforcing member is formed of a resin material, and a recess is formed in the third surface of the support plate, and a metal plate is disposed in the recess.

* * * * *